(12) United States Patent
Harrison et al.

(10) Patent No.: US 8,894,616 B2
(45) Date of Patent: Nov. 25, 2014

(54) STABILIZATION DEVICE

(75) Inventors: Robert Harrison, Milton (CA); Laura Man Yee Yu, Markham (CA); Neil Godara, Milton (CA)

(73) Assignee: Kimberly-Clark Inc., Mississauga, Ontario (CA)

( * ) Notice: Subject to any disclaimer, the term of this patent is extended or adjusted under 35 U.S.C. 154(b) by 158 days.

(21) Appl. No.: 13/139,572

(22) PCT Filed: Feb. 9, 2010

(86) PCT No.: PCT/CA2010/000143
§ 371 (c)(1),
(2), (4) Date: Jun. 14, 2011

(87) PCT Pub. No.: WO2010/081242
PCT Pub. Date: Jul. 22, 2010

(65) Prior Publication Data
US 2011/0264049 A1    Oct. 27, 2011

Related U.S. Application Data

(60) Provisional application No. 61/145,581, filed on Jan. 18, 2009.

(51) Int. Cl.
| | | |
|---|---|---|
| A61M 5/32 | (2006.01) | |
| A61M 5/00 | (2006.01) | |
| A61B 19/00 | (2006.01) | |
| A61B 17/34 | (2006.01) | |
| A61B 17/00 | (2006.01) | |

(52) U.S. Cl.
CPC ....... *A61B 19/26* (2013.01); *A61B 2017/00858* (2013.01); *A61B 17/3403* (2013.01); *A61B 2017/3407* (2013.01); *A61B 2019/267* (2013.01)
USPC ............ 604/174; 604/116; 604/178; 604/250

(58) Field of Classification Search
USPC ................. 604/174, 178, 149, 116, 167, 250; 128/DIG. 6, DIG. 26
See application file for complete search history.

(56) References Cited

U.S. PATENT DOCUMENTS

| | | | |
|---|---|---|---|
| 4,533,349 A | * | 8/1985 | Bark .............................. 604/174 |
| 4,899,756 A | | 2/1990 | Sonek |

(Continued)

FOREIGN PATENT DOCUMENTS

| | | |
|---|---|---|
| EP | 0 102 800 | 3/1984 |
| EP | 1 634 529 | 3/2006 |

(Continued)

OTHER PUBLICATIONS

International Search Report for CA2010/000143—7 pages.

(Continued)

*Primary Examiner* — Emily Schmidt
*Assistant Examiner* — Lauren M Peng
(74) *Attorney, Agent, or Firm* — Dority & Manning, P.A.

(57) ABSTRACT

A method and apparatus are disclosed for a stabilization device for maintaining a position of a medical device relative to a body surface of a patient. The stabilization device comprises a support portion that defines a groove for receiving the medical device. The groove is structured to allow for positioning of the medical device at a plurality of angles relative to the body surface of the patient. The groove has opposing wall portions for securing the medical device.

25 Claims, 30 Drawing Sheets

(56) References Cited

U.S. PATENT DOCUMENTS

| | | | |
|---|---|---|---|
| RE34,353 E * | 8/1993 | Perry et al. | 600/300 |
| 5,292,325 A * | 3/1994 | Gurmarnik | 606/108 |
| 5,873,540 A * | 2/1999 | Hardin | 242/405.1 |
| 5,911,707 A | 6/1999 | Wolvek et al. | |
| 6,106,539 A * | 8/2000 | Fortier | 606/185 |
| 6,355,028 B2 * | 3/2002 | Castaneda et al. | 606/1 |
| 6,375,017 B1 | 4/2002 | Schattner et al. | |
| 6,428,516 B1 * | 8/2002 | Bierman | 604/174 |
| 6,450,989 B2 * | 9/2002 | Dubrul et al. | 604/104 |
| 2003/0078590 A1 | 4/2003 | Errico et al. | |
| 2006/0180714 A1 | 8/2006 | Mailhot | |
| 2006/0186256 A1 * | 8/2006 | Mogensen et al. | 242/405.1 |

FOREIGN PATENT DOCUMENTS

| | | |
|---|---|---|
| WO | WO 99/25399 | 5/1999 |
| WO | WO 00/19906 | 4/2000 |
| WO | WO 00/40155 | 7/2000 |
| WO | WO 2004/020036 | 3/2004 |
| WO | WO 2004/062488 | 7/2004 |

OTHER PUBLICATIONS

Supplementary EP Search Report, May 2, 2014.

* cited by examiner

_US 8,894,616 B2_

STABILIZATION DEVICE

TECHNICAL FIELD

The invention relates to devices for supporting or anchoring medical devices during use.

BACKGROUND OF THE ART

In percutaneous medical procedures, it is often necessary to maintain the position of a medical device at a specified target location after it has been inserted. In some situations the practitioner may release the device after the device tip has been positioned at the target location. This may cause the device to pivot about the skin or other anatomical structure. This may be due to the weight of the device being greater at the proximal end. In other words a top-heavy device may be problematic due to its tendency to rotate. In some situations one or more cables extending from the distal end of the device may increase the moment of rotation about the skin or other anatomical structure. This may be a cause for concern where the tip of the surgical device is suspended in soft tissue rather than anchored in bone. The tip may move from the target location requiring re-positioning of the probe. Alternatively, treatment may be provided at an incorrect location, causing the treatment to be ineffective.

U.S. Pat. No. 5,911,707, by Wolvek et al. discloses a needle guide that ensures that an angiographic needle is inserted into a patient's femoral artery at a prescribed location angle and direction. The needle guide includes an elongated base and a support member on the upper surface of the base. The support member has a support surface which is inclined at a prescribed angle with respect to a locating plane defined by the base. Wolvek et al. also disclose that the needle guide may include a second support at the opposite end of the base, which may have a support surface inclined at an angle relative to the locating plane of the base which is different from the angle the first support member makes with the locating plane of the base. However, the device of Wolvek limits the angles at which the needle can be inserted to two specific angles. Thus there is a need in the art to provide a device which can provide support for a medical device at a multiplicity of angles. Furthermore, Wolvek does not disclose a means to adjust or fix the depth of insertion. Thus, there exists a need for a medical support device that allows a medical device to be positioned at any one of a multiplicity of angles and depth and allows the medical device to be secured in that position.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
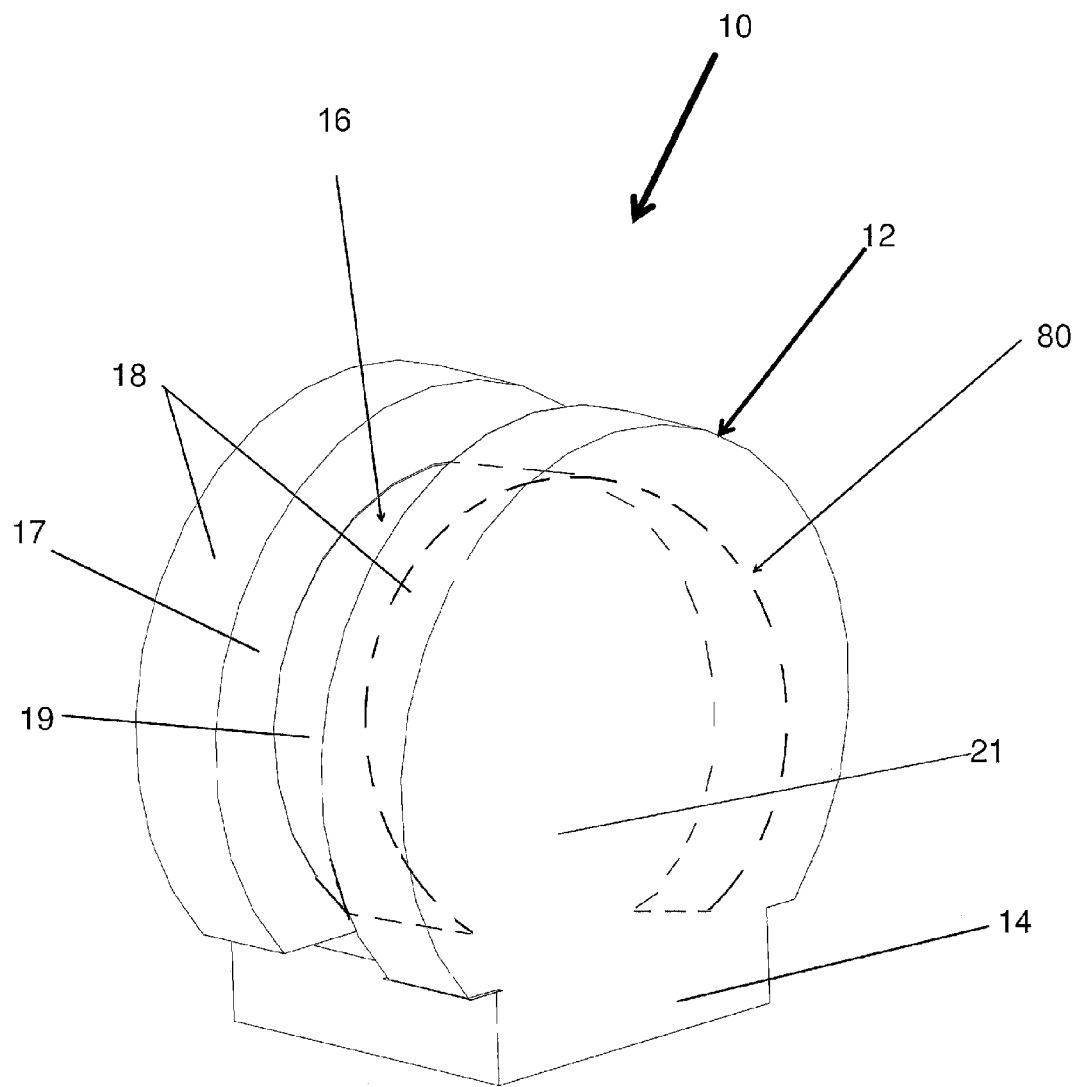
FIG. 1A is a side perspective view of a stabilization device in accordance with an embodiment of the present invention.

In one broad aspect, embodiments of the present invention comprise a stabilization device for maintaining a position of a medical device relative to a surface of a patient's body, the stabilization device comprising a support portion, said support portion defining a groove for receiving the medical device, the groove structured to allow for positioning of the medical device at a plurality of angles relative to the surface of the patient's body, the groove having opposing wall portions for securing the medical device.

As a feature of this aspect, the groove is a substantially circumferential groove. In one embodiment the groove comprises a plurality of contiguous segments of differing slope.

As a further feature of this aspect, the embodiments of the present invention comprise a stabilization device comprising a base portion, the base portion being attached to a lower surface of said support portion. In one embodiment the base is a quadruped base.

With specific reference now to the drawings in detail, it is stressed that the particulars shown are by way of example and for purposes of illustrative discussion of certain embodiments of the present invention only. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

An embodiment of the present invention comprises a stabilization device 10, as shown in FIG. 1A, for maintaining a position of a medical device with respect to a patient's skin. As shown in FIG. 1A, the stabilization device comprises a support portion 12 and a base portion 14. The support portion defines a groove 16 extending along a surface of the support portion. The groove is a continuous groove that is designed to receive a medical device. The groove extends circumferentially along a surface of the support portion. In some embodiments the groove extends substantially along the surface. In other embodiments the groove may extend at least partially along the surface. The medical device can be inserted into the recess defined by the groove. The groove is structured to allow for positioning of the medical device at a plurality of angles relative to a surface of the patient's body. The groove defines two opposing walls 18 for securing the medical device in position. Each of the opposing walls 18 comprises an inner surface 17 that functions to engage a portion of the medical device. Each of the walls 18 further comprises an outer surface 21. In one embodiment of the present invention, the cross-section of the walls 18 is substantially disk-shaped. In other embodiments the walls 18 may be square, rectangular, cylindrical or any other suitable shape. As described above, a medical device may be held in frictional engagement with the wall inner surface 17 and optionally with the groove surface 19. This allows the stabilization device to retain the medical device in its insertion position. The stabilization device functions to maintain the position of the medical device in terms of the desired angle as well the depth of insertion. In other words a medical device may be held within the groove 16 of the stabilization device 10 and may be supported at a plurality of different angles by a support 80 that forms the surface 19 of the groove 16. The stabilization device may comprise materials approved for medical device applications. In one embodiment the material may be a thermoplastic such as Acrylonitrile butadiene styrene (ABS) or a polycarbonate. In other embodiments any other suitable material may be used. In some embodiments, the stabilization device 10 comprises a radiolucent material that is not visible under radiographic imaging. This allows the practitioner to obtain a clear radiographic image of any medical devices being used in the procedure. The stabilization device may be formed by injection moulding or any other suitable means of manufacturing.

Figure 1B:
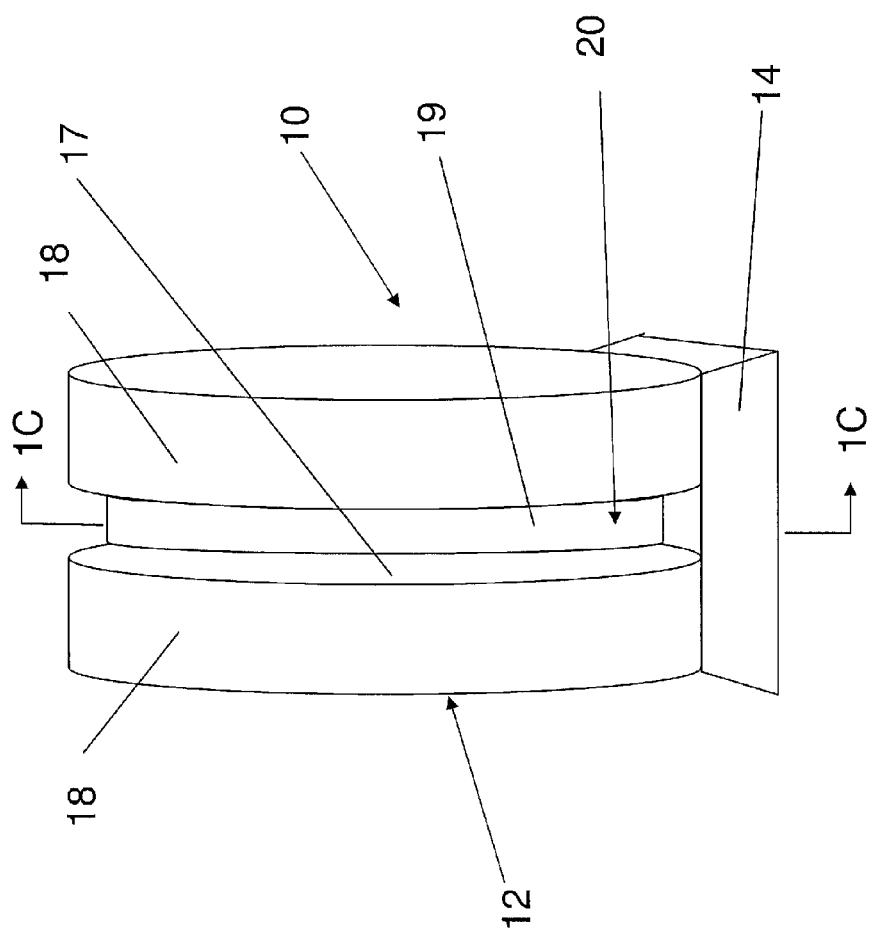
FIG. 1B is a front perspective view of a stabilization device in accordance with an embodiment of the present invention.
Figure 1C:
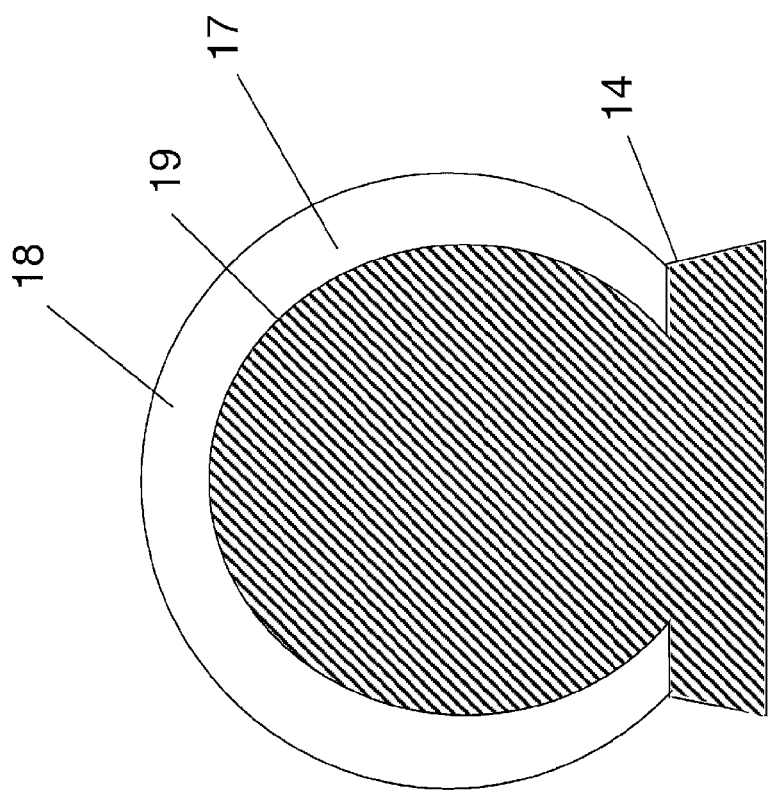
FIG. 1C is a cross-sectional view taken along the line 1C-1C of FIG. 1B.
Figure 1D:
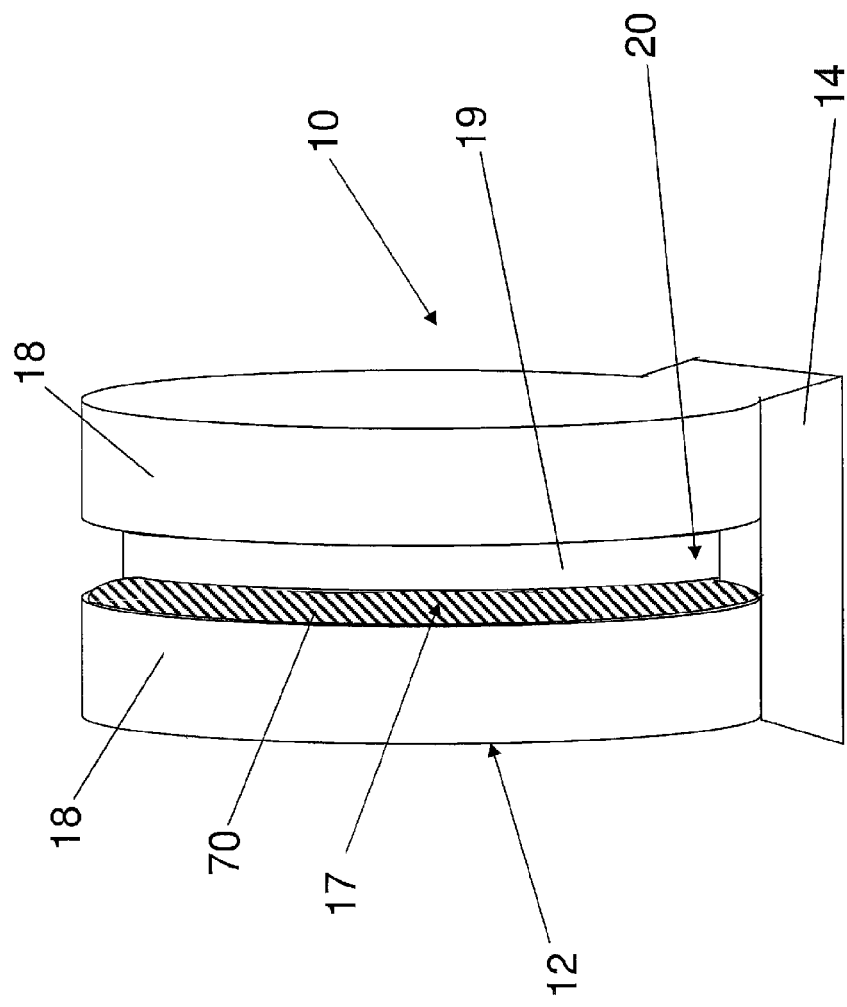
FIG. 1D is a front perspective view of a stabilization device in accordance with an alternate embodiment of the present invention.

Referring now to FIG. 1B, in one embodiment of the present invention, the groove 16 is a circular circumferential groove 20. The groove extends circumferentially along a circular surface of the stabilization device as shown in FIGS. 1B and 1D. FIG. 10 illustrates a cross-section of the stabilization device taken through the groove, along a plane that is parallel to the walls 18. The stabilization device has a circular cross-section as indicated by the groove surface 19 in FIG. 10.

In other words the support 80 formed by the groove 20 has a substantially circular radial cross-section as shown in FIG. 10. The circular circumferential groove 20 allows a medical device be inserted at any angle such that the medical device is substantially at a tangent to the curved surface 19 of the groove. In other words it allows the medical device to be positioned at any point of contact with the surface 19 of the groove such that the medical device is at a tangent. In some embodiments the medical device is held in frictional engagement within the walls 18 and may not be in contact with the surface 19 of the groove. In some embodiments the groove may comprise a surface that may be elliptical, ovoid or any other shape. In one specific example, the outer surface 21 of the walls has a diameter of about 24 mm. The groove 30 has a lateral or cross-sectional width of about 5.54 mm between the two wall surfaces 17. The groove surface 19 is substantially circular with a diameter of about 17.8 mm. In one embodiment of the present invention as shown in FIG. 1D, the inner wall surfaces 17 may be rough and may comprise a plurality of projections or grooves 70. These grooves 70 may help increase the frictional force between the wall inner surface 17 and the medical device and may help to secure the medical device at a desired position.

Figure 2A:
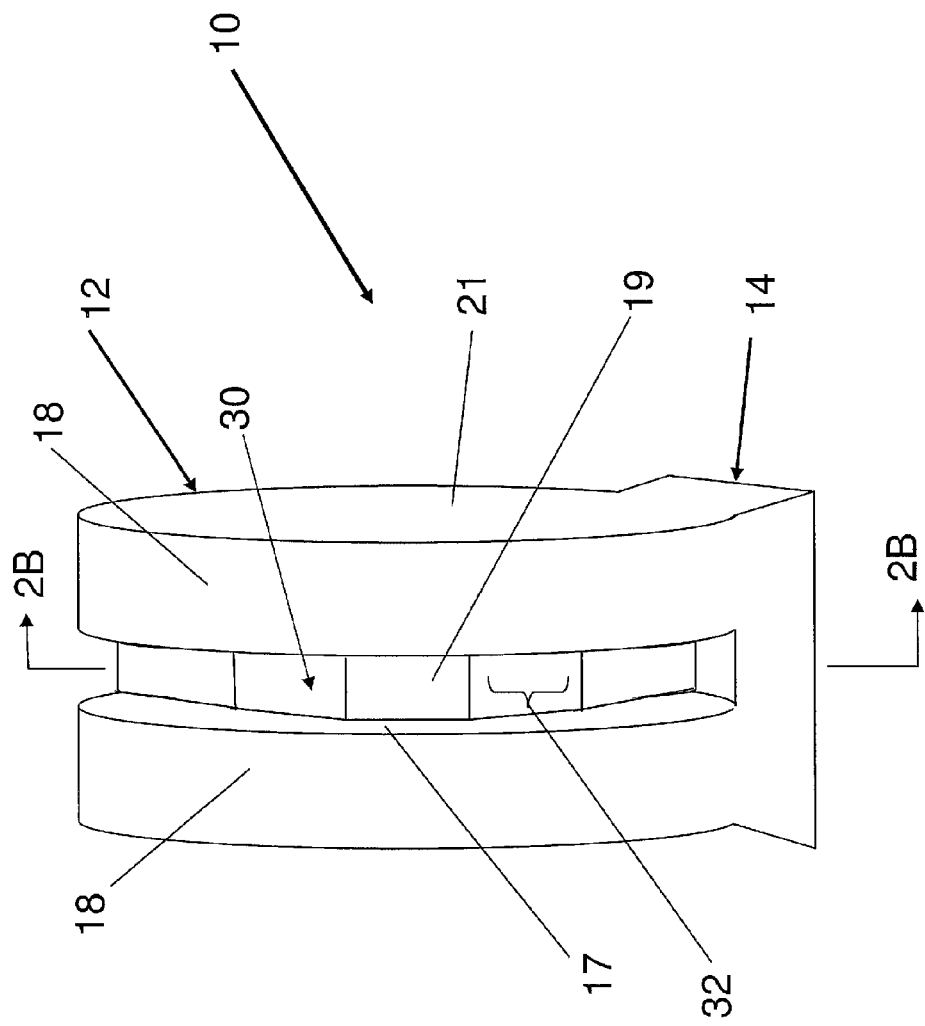
FIG. 2A is a front perspective view of a stabilization device in accordance with an embodiment of the present invention.
Figure 2B:
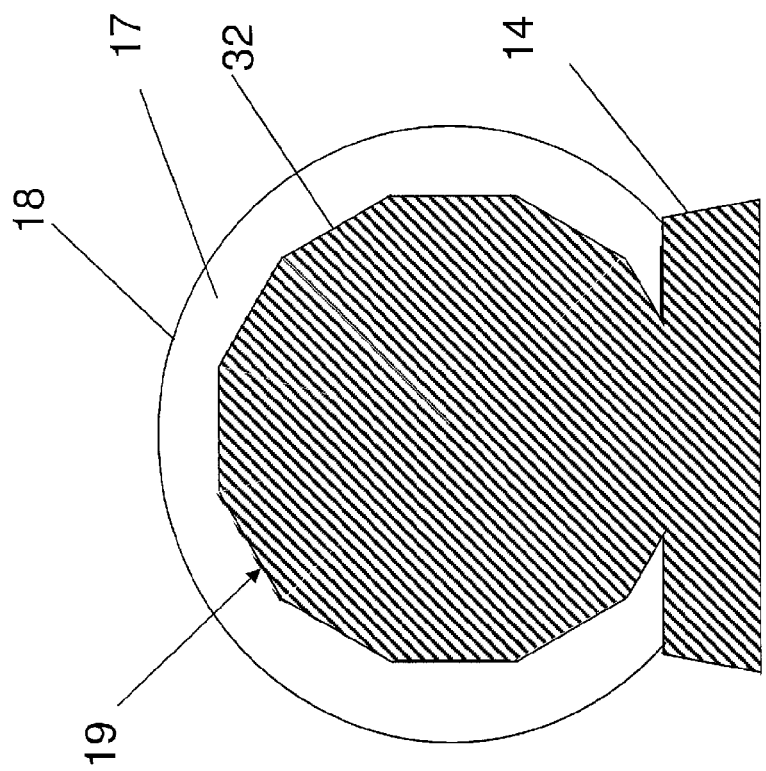
FIG. 2B is a cross-sectional view taken along the line 2B-2B of FIG. 2A.

In an alternate embodiment as shown, for example in FIG. 2A, the circumferentially extending groove may not have a uniformly varying slope and may comprise a plurality of contiguous segments 32 of differing slopes. In one specific embodiment, as shown in FIG. 2A, the contiguous segments of different slopes form a surface 19 that has a cross-section that may generally be in the shape of a polygon. The groove is a polygonal circumferential groove 30, where each segment 32 allows the medical device to be positioned at a specific angle with respect to a surface of the patient's body. The cross-section of the stabilization device taken along the groove, along a plane that is parallel to the walls 18, is substantially polygonal in shape as illustrated in FIG. 2B. In other words the support formed by the groove 30 has a substantially polygonal radial cross-section. In some examples the cross-section of the stabilization device along the groove may be hexagonal, octagonal or any other similar shape. In one specific example, the stabilization device has a polygonal circumferential groove 30 with substantially disk-shaped walls as illustrated in FIG. 2A.

In embodiments of the present invention as shown in FIGS. 1 and 2, the opposing wall portions 18 allow a medical device to be secured by the support portion 12. As outlined above the medical device is placed in frictional engagement within the groove. In one embodiment this frictional force opposes the moment generated by the handle of the device or by any cabling that may extend from the proximal portion of the device.

Figure 3:
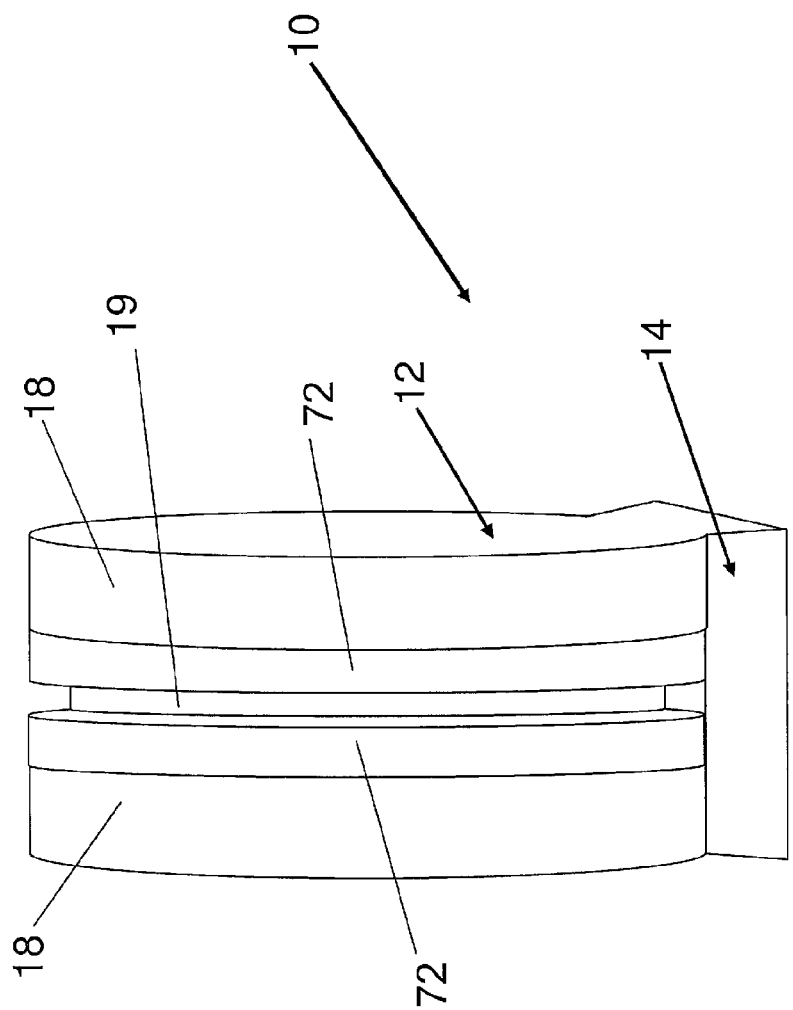
FIG. 3 is a front perspective view of a stabilization device in accordance with an alternate embodiment of the present invention.

As illustrated in FIG. 3, in one embodiment of the present invention, the opposing wall segments may comprise a coating 72 of an elastomeric material to increase the ability of the wall portions 18 to grip a medical device. The coating 72 is applied to the inner wall surfaces 17. In some embodiments the coating 72 may also be applied to the surface 19 of the groove. The coating 72 may comprise elastomeric materials, including but not limited to, rubbers such as synthetic rubber, thermoplastic elastomer (TPE), silicone elastomer and polyurethane elastomer. In some embodiments the elastomer coating 72 may comprise silicone. In one specific example, the silicone is a medical grade silicone. In an alternate embodiment, the elastomer coating 72 may comprise a synthetic rubber such as polychloroprene (neoprene). Alternatively, a thermoplastic elastomer such as Santoprene™ may be used. In still another example, the coating 72 may comprise a Styrene-based thermoplastic elastomer (TPE). The elastomer coating may be applied through the process of overmolding onto the stabilization device. Alternatively, the coating may be added to the stabilization device through a 2-shot moulding process. In another embodiment, the elastomer coating may be in the form of a pad that may be adhesively applied to the inner wall surfaces 17.

In one specific example the stabilization device 10 comprises a coating 72 of silicone on the inner wall surfaces 17. This coating 72 may be applied in the form of a spray coating, where multiple coats may be applied to provide the desired thickness. In other embodiments the walls of the support portion 12 may be dip-coated with silicone to form the coating 72. In an alternate embodiment the wall portions may be fabricated substantially entirely of silicone. In some embodiments the coating 72 may be in the form of a silicone pad that may be adhesively attached to each of the inner wall surfaces 17 and/or the surface 19 of the groove. The silicone pad may be formed from a sheet of silicone. A die cut mold may be used to stamp out the desired shape of the silicon pad that is suited for placement along the inner wall surfaces 17. Alternatively, the pads may be formed from any other suitable elastomer material. The pads acts as a gripping surface and enhance the frictional force between the stabilization device and the medical device that is inserted into the groove. Both, the distance between the pads and the durometer of the pads can be designed to permit medical devices of different gauges to be inserted into the groove and to be supported by the stabilization device. In one example, the pads have a durometer of about 30-40 Shore A. This provides for malleability and compressibility of the elastomer material allowing medical devices of varying gauges to be inserted into a single stabilization device. In other words, pads with a set thickness may allow a single stabilization device to hold multiple gauges of medical devices. The pads function similarly to break pads to hold the medical device in place. For example medical devices with 22G-16G diameter can be supported by a single stabilization device. In other embodiments, an elastomer material with a durometer less than 30 Shore A or greater than 40 Shore A may be used. In one specific example a silicone pad with a durometer of 35 Shore A is used. In an alternate embodiment the pad may have a plurality of 'bumps' or projections on the surface. In other words the pads can be texturized and may have a raised texture to increase the ability of the pads to grip a medical device. This may be advantageous in instances where the coating may have come in contact with fluid, for example such as blood, making it harder for the pads to grip the medical device. The raised texture of the pads may increase the gripping force of the pads, allowing a medical device to be held in place between them in the presence of fluid.

Figure 4:
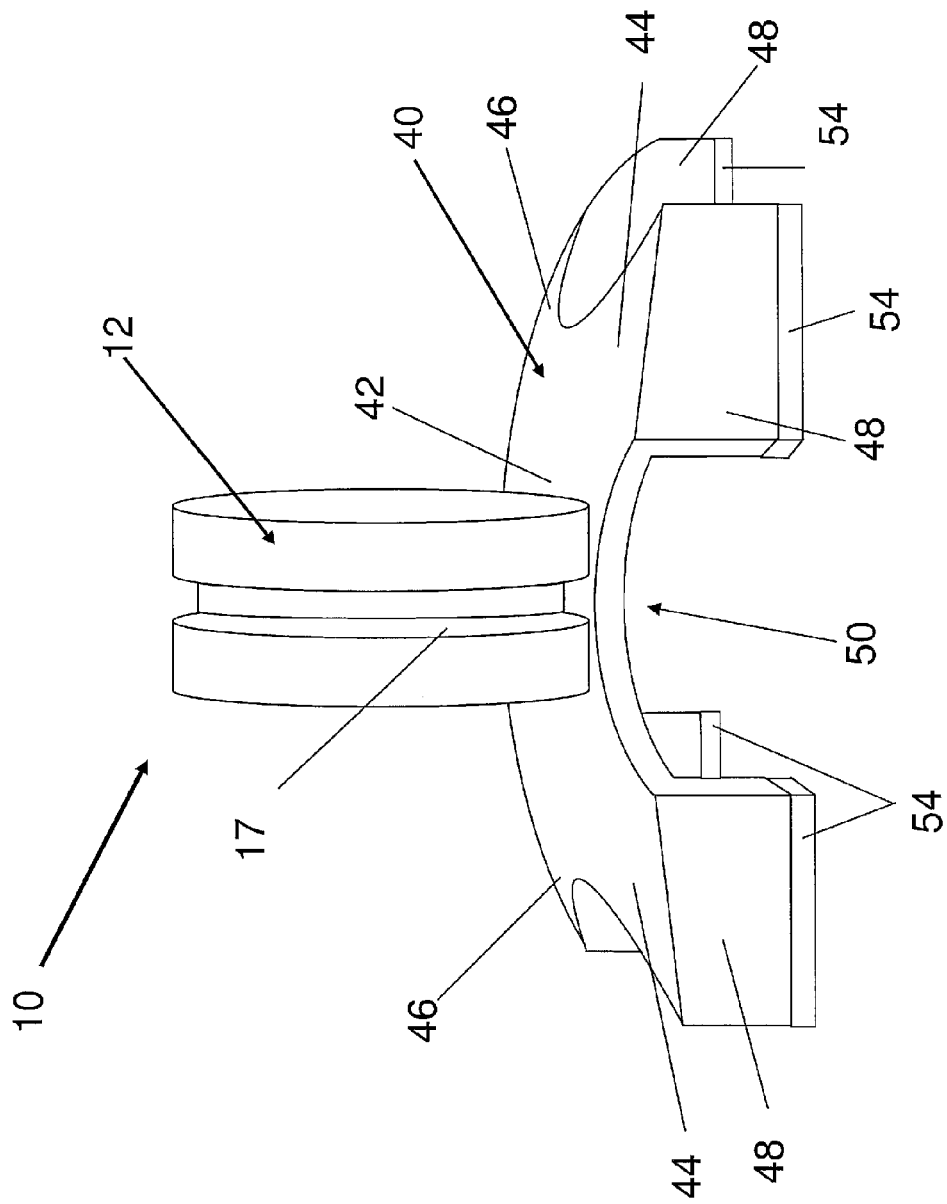
FIG. 4 is a front perspective view of a stabilization device with a quadruped base in accordance with an embodiment of the present invention.
Figure 7:
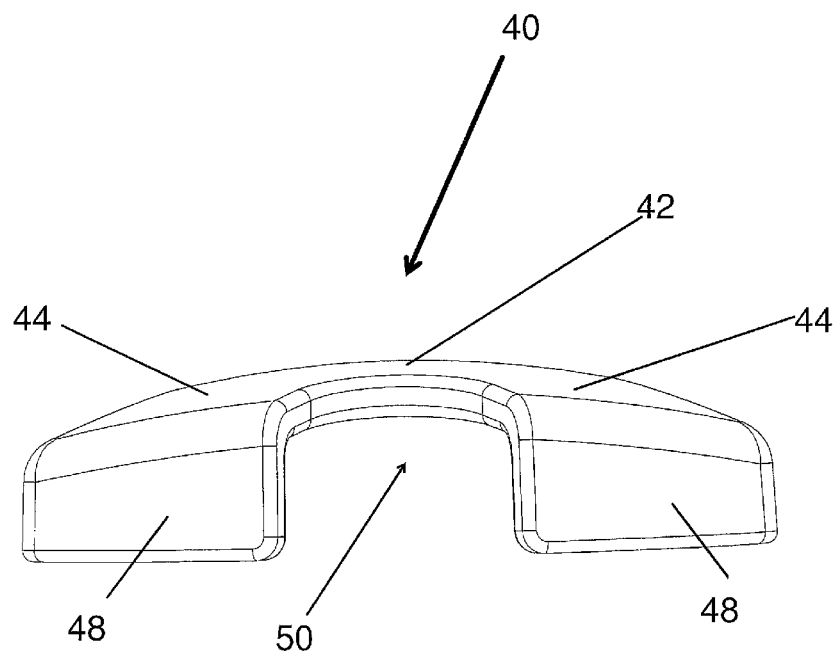
FIG. 7 is a front view of a quadruped base in accordance with an embodiment of the present invention.

In an embodiment of the present invention, the support portion 12 is attached to a base portion 14 along its lower surface. In alternate embodiments the base portion 14 extends integrally from the support portion 12. In one embodiment of the present invention, the base portion 14 is substantially rectangular as illustrated in FIG. 1. In one specific example of this embodiment, the base portion 14 is dimensioned to have a length of about 14.5 mm, a width of about 14 mm and a thickness of about 3-4 mm. In another embodiment as shown in FIG. 1B the base may be frustum shaped having slanting side edges. In some embodiments, the base portion 14 is wider than the support portion 12 and is dimensioned to have a greater surface area for stability. In one embodiment of the present invention, the base portion comprises a substantially flat platform with a plurality of horizontally extending legs or projections, each of which ends in a foot portion. In one such embodiment of the present invention, the base is a quadruped base 40 as illustrated in FIG. 4. The quadruped base 40 has a substantially flat platform 42 comprising at least four horizontal projections or legs 44, 46, each of which terminates in a vertical foot portion 48. The wide base allows the stabilization device 10 to be positioned securely on the patient's skin. This feature may be advantageous when placing the stabilization device on contoured surfaces on the patient' body. A wider base may prevent the stabilization device 10 from slipping or sliding off a contoured surface, for example a patient's back. The feet 48 on the base member allow the base platform 42 to be elevated from the patient's skin. This may allow for easier placement as the feet 48 can be positioned around a bony surface allowing the platform 42 to be raised slightly above it. In one embodiment the feet 48 may allow the base platform 42 to be raised between about 3 mm-5 mm above the surface of the patient's skin. In some embodiments the height of the feet 48 may vary along their length as illustrated in FIG. 7. In one embodiment of the present invention the feet 48 may further comprise a coating 54 on the lower surface thereof to help prevent the stabilization device 10 from tipping or sliding across a surface of the patient's body. The coating may comprise elastomeric materials, including but not limited to, rubbers such as synthetic rubber, thermoplastic elastomer, silicone elastomer and polyurethane elastomer. In some embodiments the elastomer coating may comprise silicone. In one specific example, the silicone is a medical grade silicone. Alternatively the coating may comprise of a synthetic rubber such as polychloroprene (neoprene) or a thermoplastic elastomer such as Santoprene™ In an alternate embodiment the feet may be comprised entirely of silicone. In another example the feet may comprise a coating of a Styrene-based thermoplastic elastomer. In a still another embodiment the coating may comprise any other material that provides anti-skidding effects.

Figure 5:
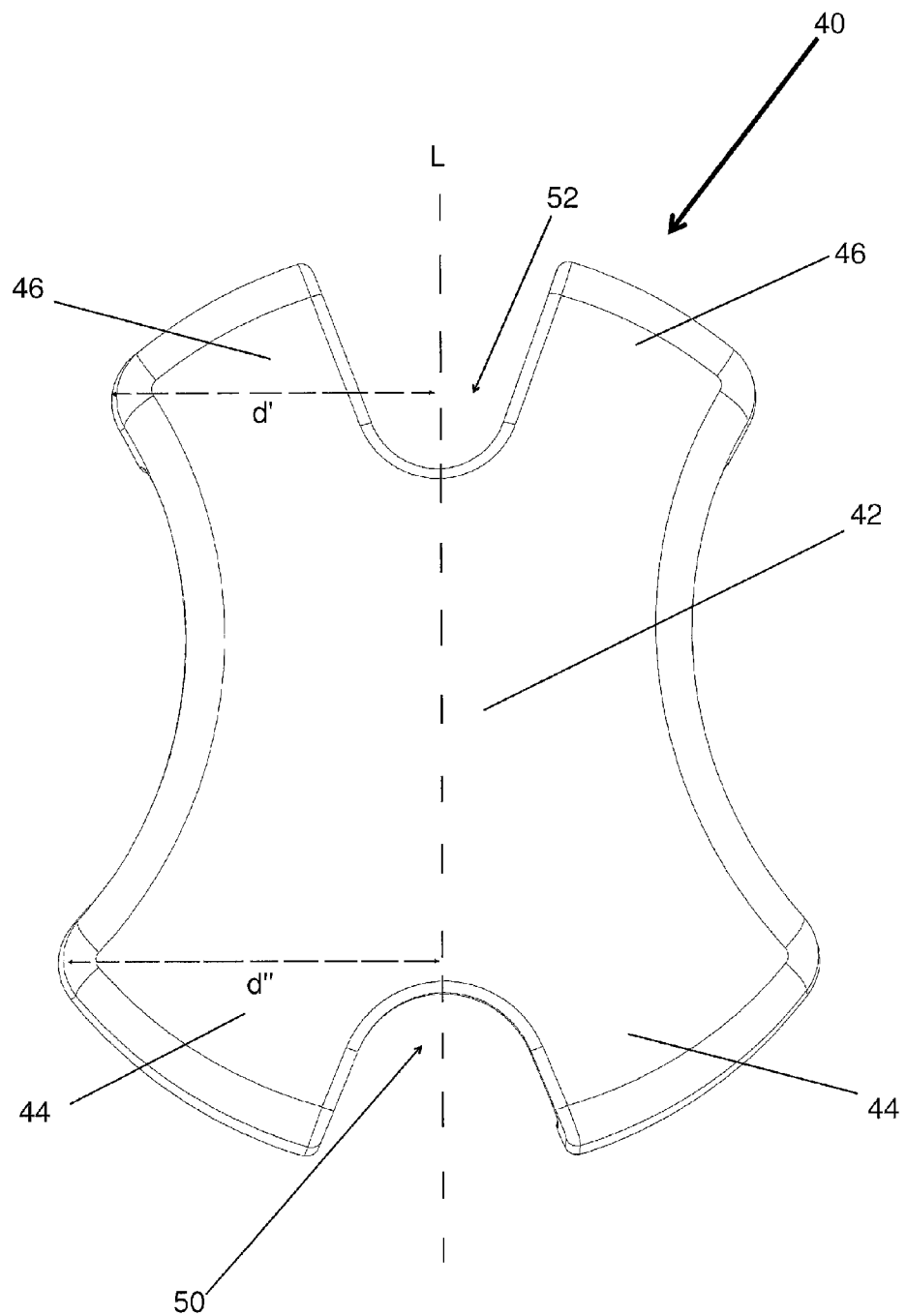
FIG. 5 is a top view of a quadruped base in accordance with an embodiment of the present invention.
Figure 6:
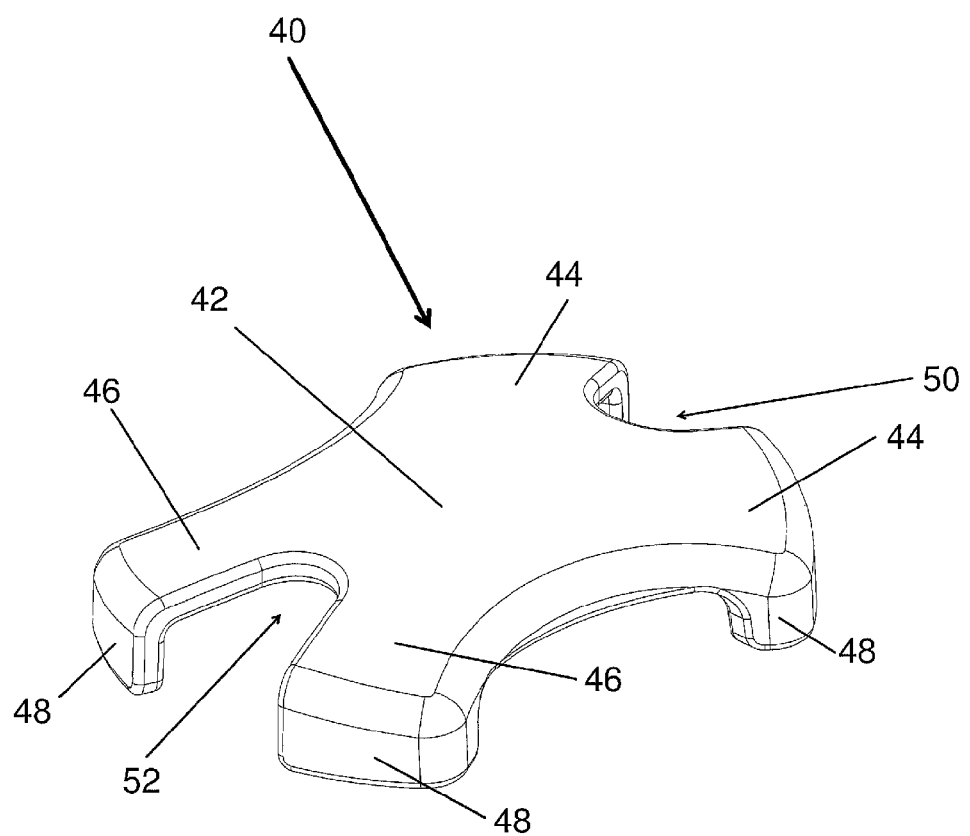
FIG. 6 is a side perspective view of a quadruped base in accordance with an embodiment of the present invention.

In accordance with one embodiment of the present invention, the stabilization device 10 has a wide base, allowing it to support a top-heavy medical device and provide stability. The base portion 14 allows for lateral stability of the stabilization device 10 during use and prevents the stabilization device from tipping onto its side. Furthermore, the base portion 14 also provides caudal support and prevents the stabilization device 10 from tipping backwards. The two front legs 44 extending from the front portion of the platform help prevent lateral displacement of the stabilization device 10. The two rear legs 46 extending from the back portion of the platform, prevent it from tipping backwards. The rear legs 46 may also prevent the stabilization device 10 from tipping onto its side. In some embodiments, the two front legs 44 may extend further outwards than the two rear legs 46 as illustrated in FIG. 5 The front legs 44 extend further away from the central axis L as shown by distance d" compared to the rear legs 46 that extend a shorter distance d' from the central axis L. This provides for greater lateral stability. In one embodiment of the present invention, the quadruped base 40 is structured to allow the medical device to have clear access to the patient's skin. The front two legs 44 form a channel 50 or opening between them allowing a medical device to be inserted or advanced freely without any hindrance. In some embodiments, a depth stopper may be used in conjunction with a medical device in order to mark the penetration depth of the medical device. The channel 50 defines a clearance for the insertion and use of a depth stopper. In one specific example the channel 50 is an arcuate channel as illustrated in FIGS. 4-6. In some embodiments the rear two legs 46 may also define a channel or opening 52 between them defining a clear passage for the insertion of a medical device. In one embodiment, the support portion 12 may be located substantially centrally with respect to the base portion 14, allowing a medical device to be inserted and held within the groove 16 such that it passes either through the channel 52 defined by the rear legs 46 or the channel 50 defined by the front legs 44. In another embodiment the support portion 12 may be positioned on the base portion 14 such that it is adjacent to the channel 50 defined by the front legs 44. In an alternate embodiment the support portion 12 may be positioned on the base portion 14 such that is adjacent to the channel 52 defined by the rear legs 46.

Figure 8A:
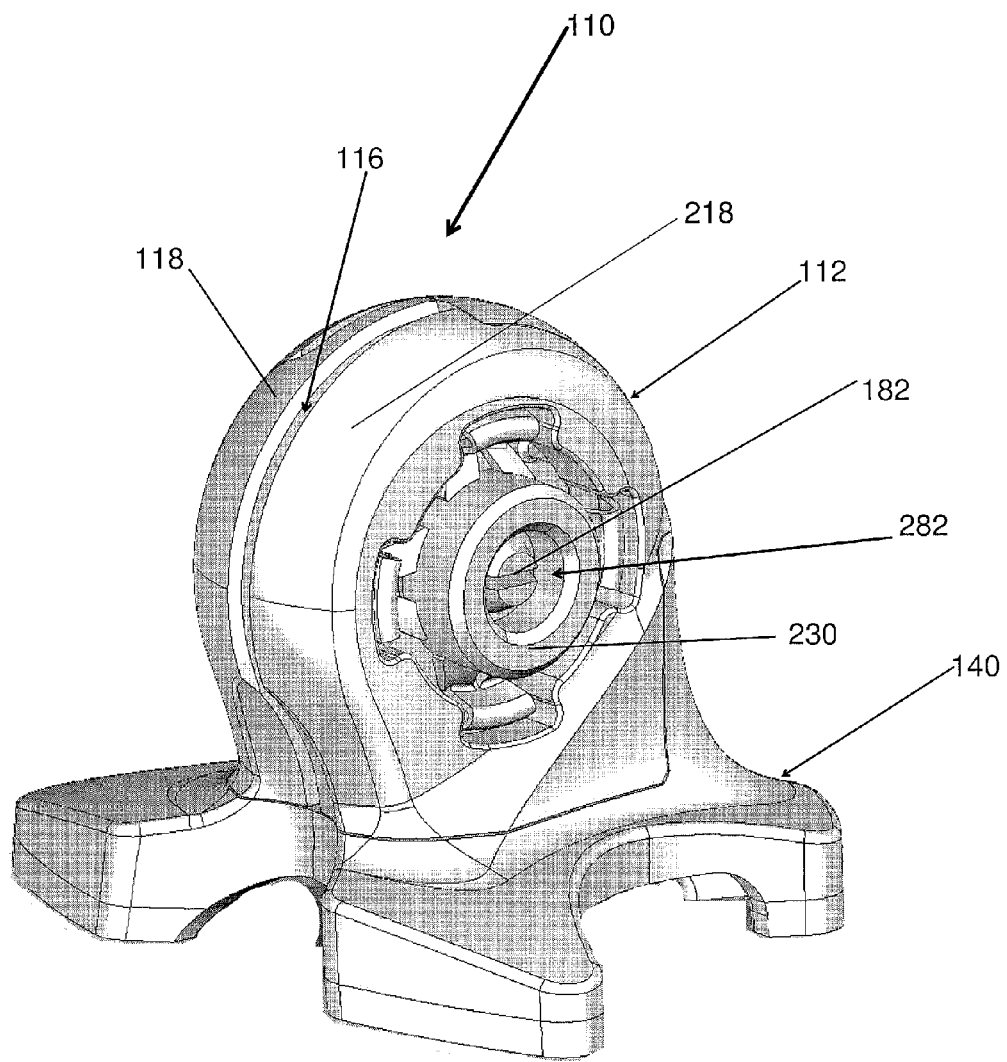
FIG. 8A is a side perspective view of a stabilization device in accordance with an alternate embodiment of the present invention.
Figure 8B:
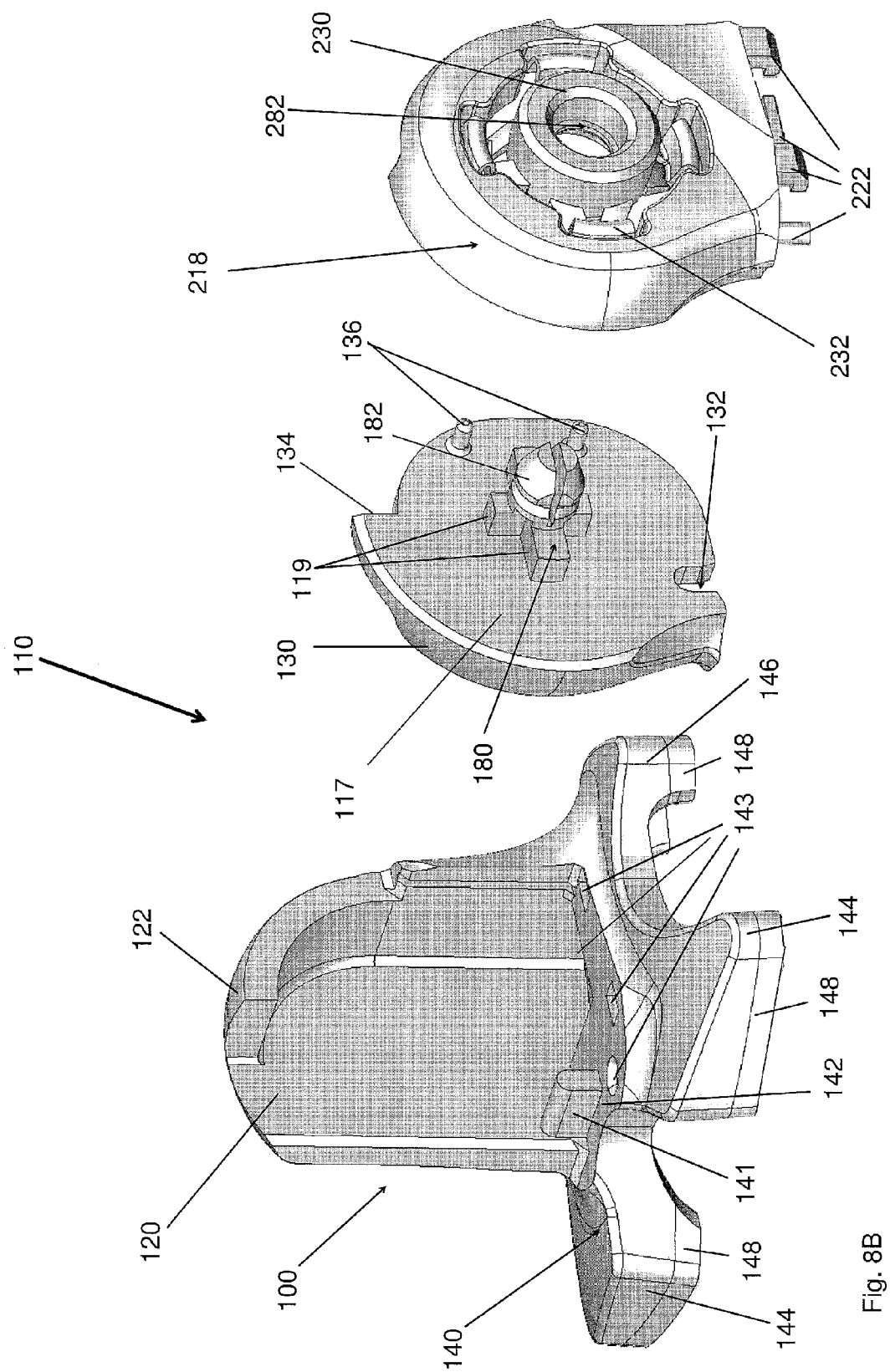
FIG. 8B is an exploded view of a stabilization device in accordance with an embodiment of the present invention.
Figure 8C:
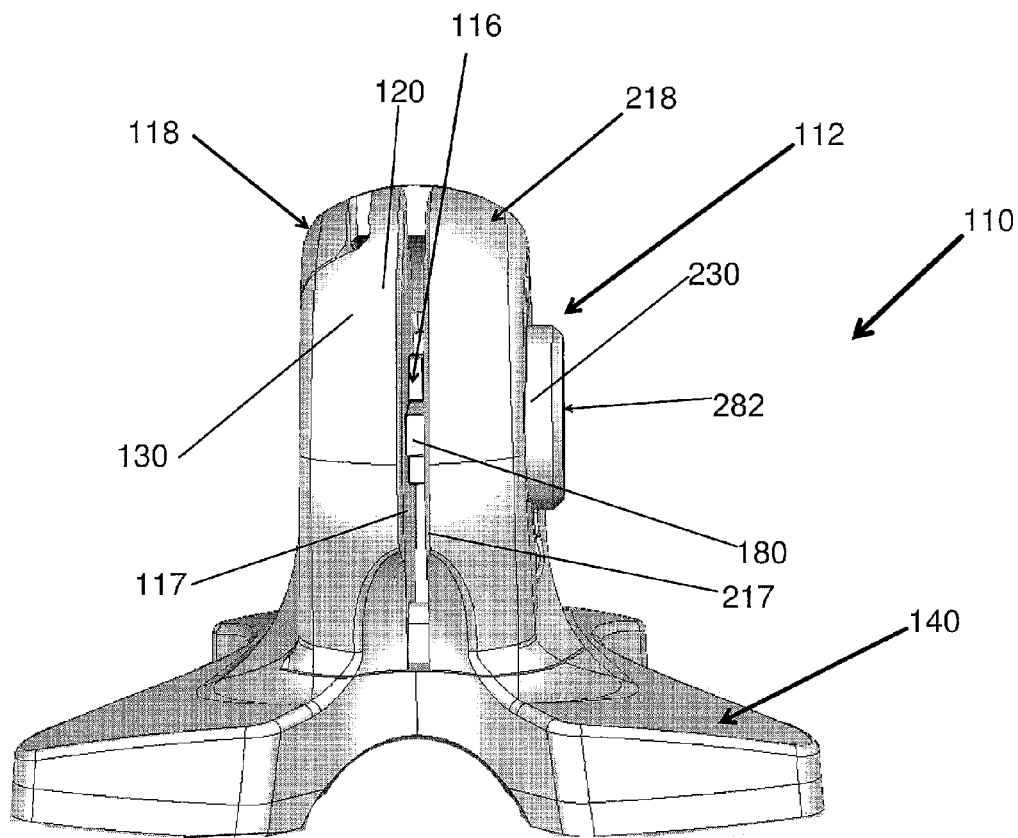
FIG. 8C is a front perspective view of a stabilization device in accordance with an embodiment of the present invention.
Figure 8D:
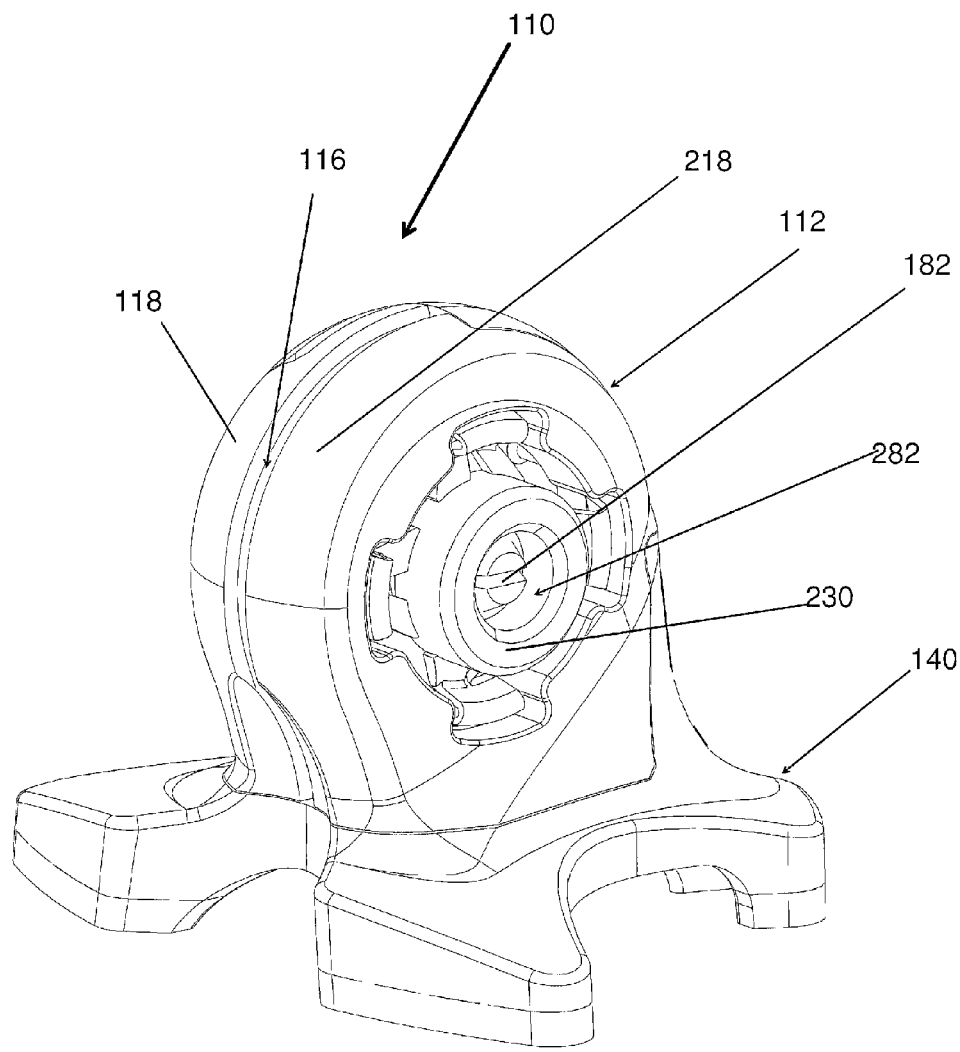
FIGS. 8D-DF are line drawings of the views shown in FIGS. 8A-8C.
Figure 8E:
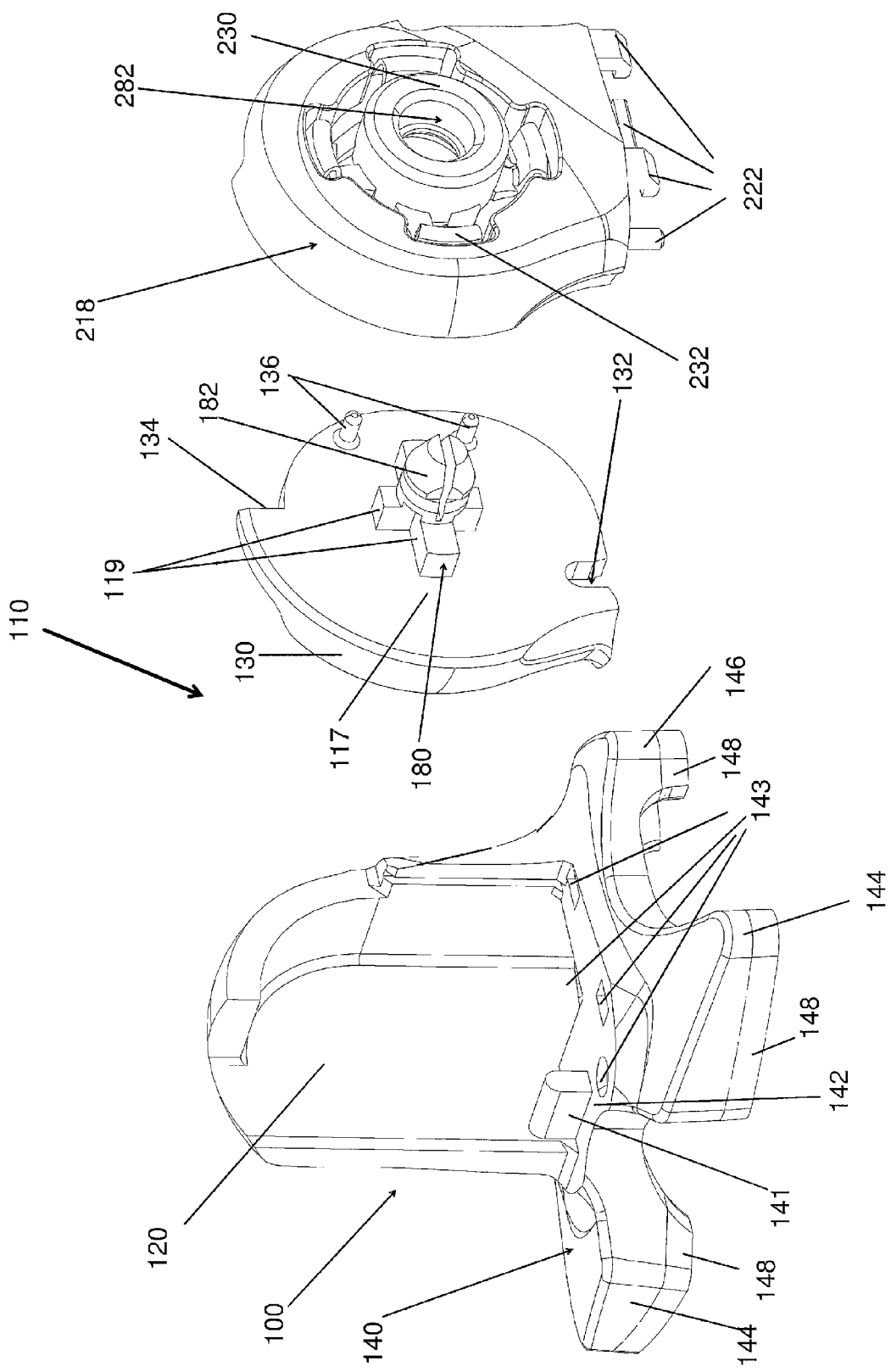
Figure 8F:
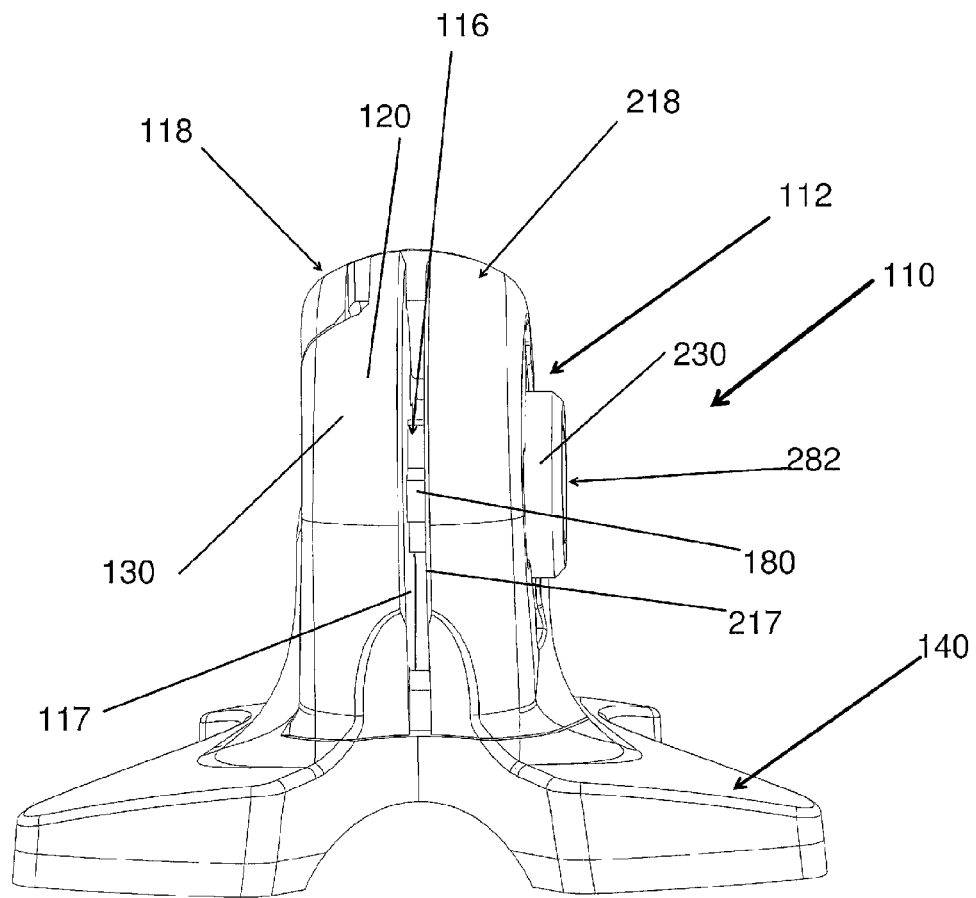
Figure 9A:
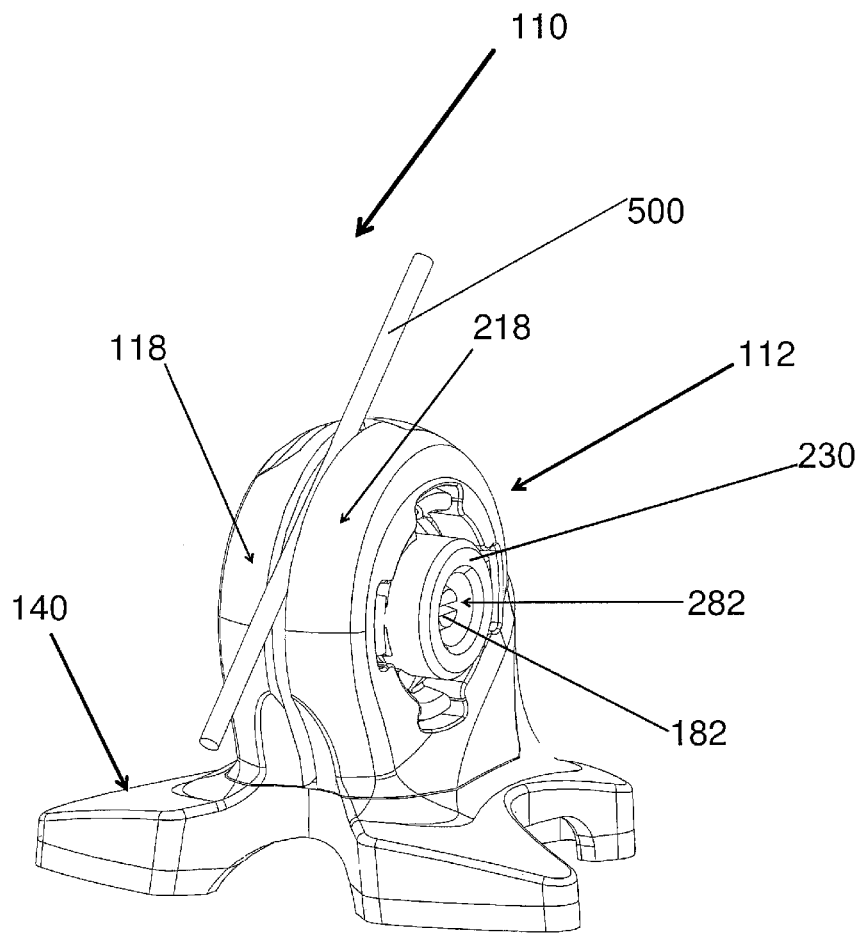
FIG. 9A is a front perspective view of a stabilization device in accordance with an embodiment of the present invention.
Figure 9B:
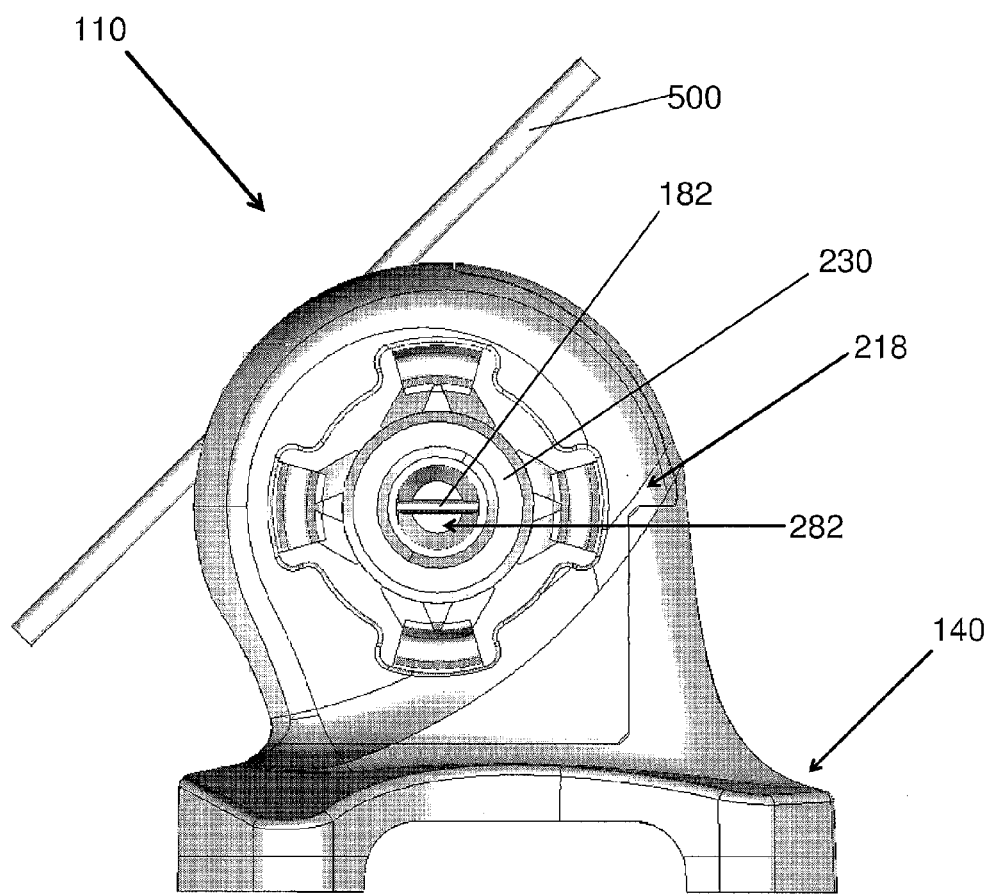
FIG. 9B is a right side view of a stabilization device in accordance with an embodiment of the present invention.
Figure 9C:
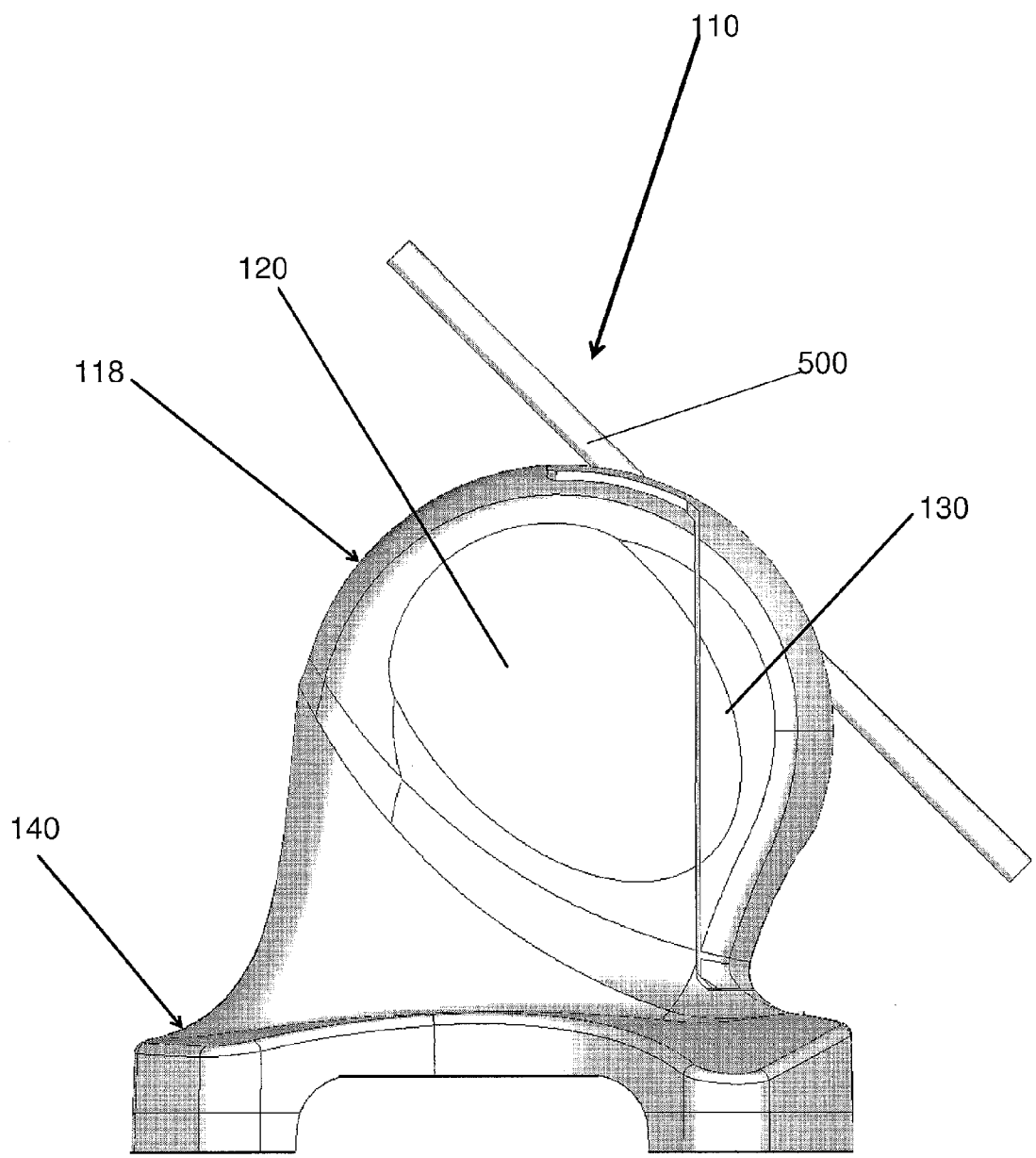
FIG. 9C is a left side view of a stabilization device in accordance with an embodiment of the present invention.
Figure 9D:
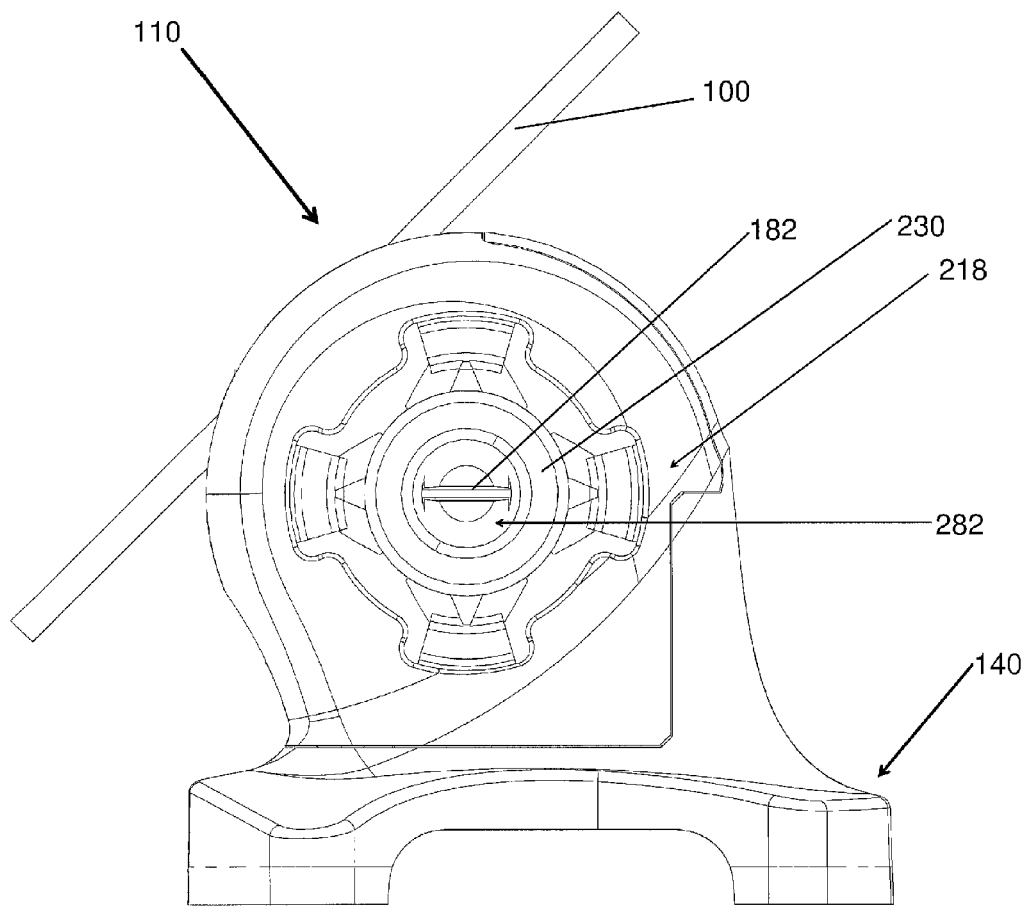
FIGS. 9D-9E are line drawings of the views shown in FIGS. 9B-9C.
Figure 9E:
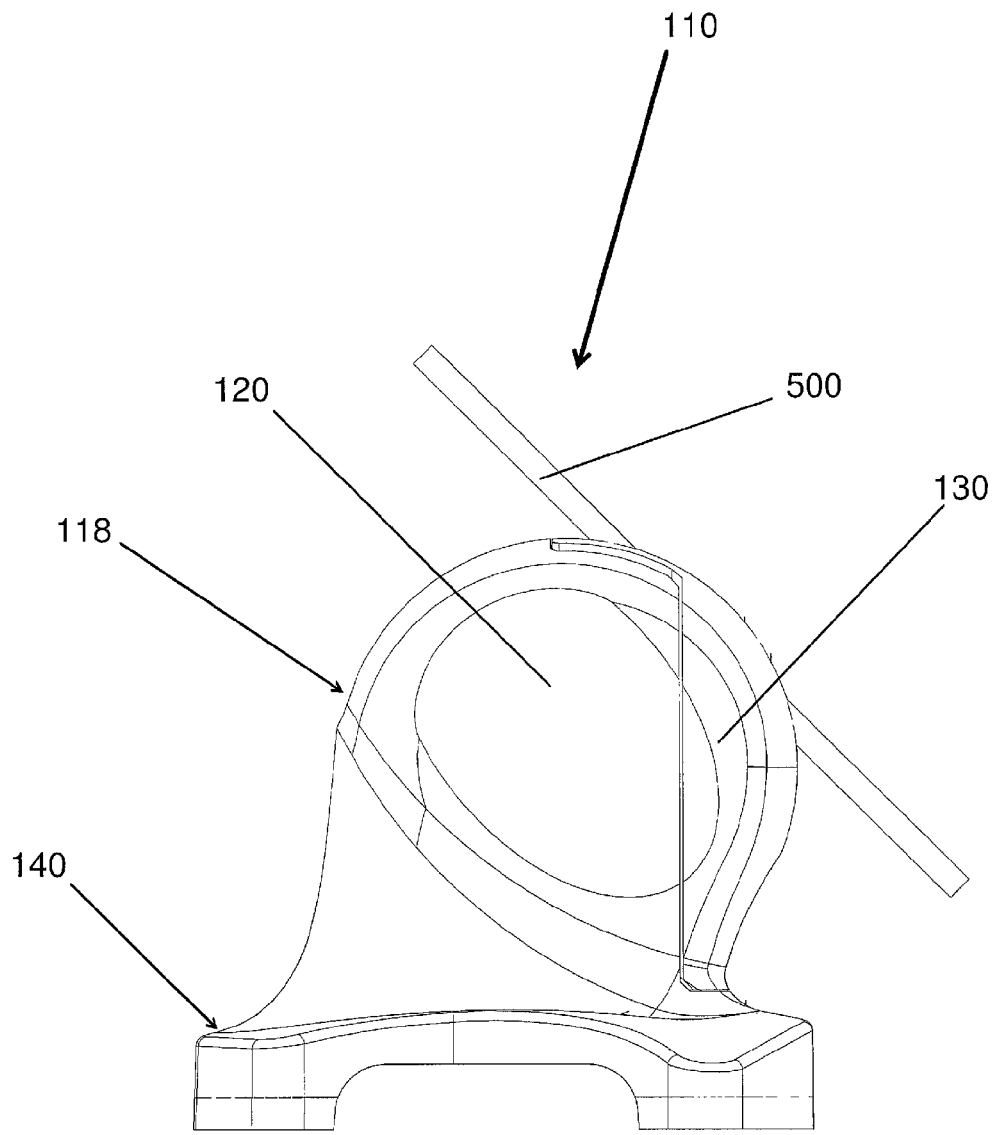

Referring now to FIGS. 8A-8C, in one embodiment of the present invention, a stabilization device 110 comprises a clamping means. The stabilization device 110 comprises a support portion 112 that is connected to a quadruped base portion 140. As shown in FIG. 8A, the support portion 112 comprises two opposing walls comprising a first wall 118 and a second wall 218. As shown in FIG. 8B, the first wall 118 comprises a fixed wall portion 120 and a moveable wall portion 130. The moveable wall portion 130 is partially received within the fixed wall portion 120. In some embodiments the fixed wall portion 120 further comprises a curved posterior wall 122. The fixed wall portion 120 is connected to a quadruped base 140, and in combination with the base 140 forms a housing 100. The moveable wall portion 130 is dimensioned to fit within the housing and can slide laterally within the housing. The moveable wall portion 130 comprises a channel 132 for receiving a projection 141 located on the base 140. The projection 141 is located substantially adjacent to the fixed wall portion 120. The channel 132 allows the moveable wall portion 130 to slide laterally along the projection 141. The moveable wall portion 130 further comprises a posterior edge 134 that allows the moveable wall portion 130 to slide smoothly along the edge of the curved posterior wall 122 of the fixed wall portion 120. The moveable wall portion 130 further comprises an inner wall surface 117 for engaging with a medical device. The moveable wall portion 130 still further comprises a support 180. One end of the support 180 is integrally connected to the lateral inner surface 117 of the moveable wall portion 130. Whereas, an opposing end of the support 180 is received within an axial bore 282 within the second wall 218. In some embodiments, the opposing end of the support 180 may comprise a button 182. The button engages with the bore 282 within the second wall portion 218 and locks with a press-fit mechanism. In other embodiments, any alternate means may be used in order to attach the support 180 to the second wall 218. In some embodiments the support 180 may have a substantially circular radial cross-section. In other embodiments the support 180 may have a substantially cross-shaped radial cross-section. In other embodiments the radial cross-section of the support may be polygonal or any other suitable shape. In some embodiments the surface 117 of the moveable wall portion 130 may additionally comprise a plurality of pins 136. The pins allow the moveable wall portion 130 to remain vertically aligned with the second wall 218. In other words, the pins 136 prevent the moveable wall portion 130 from tilting or bowing. Alternatively, in some embodiments the moveable wall portion 130 may comprise a raised bar instead of pins 136, that functions similarly to the pins 136, by allowing the moveable wall portion 130 to remain vertically aligned with the second wall 218.

The second wall 218 comprises a resilient wall portion 230 that defines the axial bore 282 for receiving the button 182 of the support 180. The resilient wall portion 230 comprises a plurality of hinges 232 which flex allowing the resilient wall portion 230 to temporarily deform when force is applied axially. This allows the resilient wall portion 230 to move laterally towards the fixed wall portion 120 of the first wall 118. When the force is removed, the resilient wall portion 230 is biased to return to its original position. The second wall 218 further comprises an inner wall surface 217 (See FIG. 8C) for engaging with a medical device. In some embodiments, the second wall 218 is removably connected to the base 140. In one example, the second wall 218 comprises a plurality of hooks and pins 222 on its lower surface that engage with the base 140 of the housing 100. In one example, the hooks and pins 222 are received within undercuts 143 in the base 140 and engage with the undercuts 143 in a snap fit configuration. In some embodiments the second wall 218 may be integrally connected to the base 140. The base 140 comprises a flat platform 142 comprising at least two front horizontal legs 144, and at least two rear horizontal legs 146, each of which terminates in a vertical foot portion 148.

As illustrated in FIGS. 8A-8F, a groove 116 is defined by the support 180, the inner wall surface 117 of the moveable wall portion 130 of the first wall 118, and the inner wall surface 217 of the second wall 218. The groove 116 comprises a groove surface 119 which is also defined as the external surface of the support 180. In some embodiments the groove 116 extends at least substantially completely along the support 180. In some embodiments the groove 116 extends at least partially along the support 180. The support 180 allows the medical device to be positioned along the groove 116 at a plurality of angles with respect to a vertical axis of the support member 112. The medical device is held in frictional engagement between the surfaces 117 and 217 of the first and second wall respectively. Additionally, the medical device may be inserted into the groove 116 such that it is also supported by the support 180. FIGS. 9A-9E, illustrate one example where a medical device 500 is inserted into the support portion 112 at an angle of 45 degrees with respect to the vertical axis. In an alternate example, a medical device 500 may be inserted at an angle of 0 degrees with respect to the vertical axis of the support member 112.

Figure 10A:
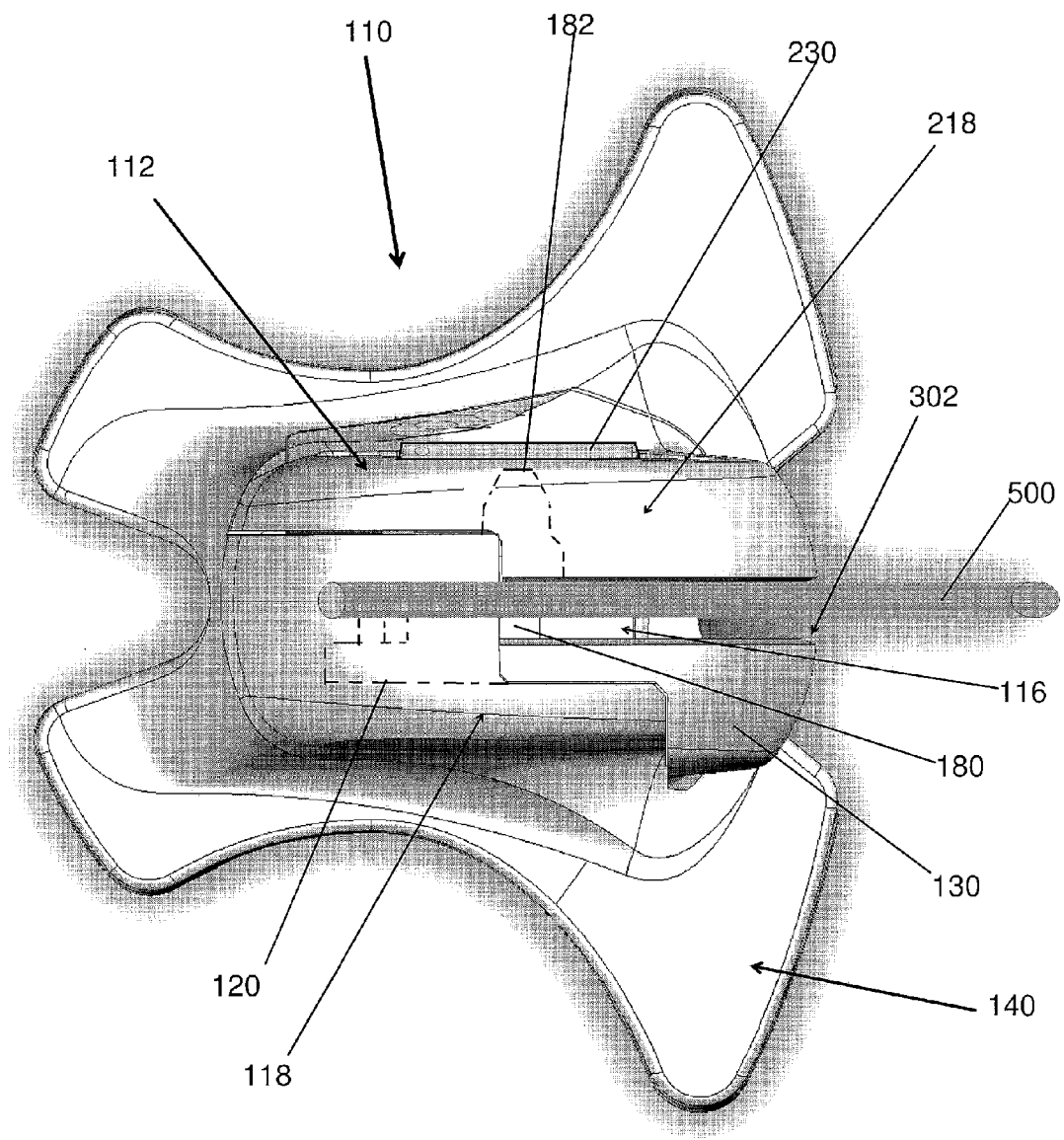
FIG. 10A is a top view of a stabilization device wherein the support portion is in an open configuration, in accordance with an embodiment of the present invention.

With reference now to FIGS. 10A-10D, and in accordance with an embodiment of the present invention, the stabilization device 110 comprises a support portion 112 operable to move between an open configuration and a closed configuration. FIG. 10A shows a stabilization device 110, where the support portion 112 is an open configuration. When an axial force is applied to the button 182 on one end of the support 180, a gap 302 between the moveable wall portion 130 and the second wall 218 widens. This allows a medical device to be received within the groove 116. The support 180 is connected to the resilient wall portion 230 such that when the button 182 on the support 180 is depressed, it causes the resilient wall portion 230 to flex towards the first wall 118. This allows the support 180 to slide axially towards the fixed wall portion 120. Since the moveable wall portion 130 is integrally connected to the support 180, the movement of the support 180 is translated to the moveable wall portion 130. The moveable wall portion 130 slides axially or laterally towards the fixed wall portion 120 such that the gap 302 between the moveable wall portion 130 and the second wall 218 increases. The gap 302 is sufficient to allow a medical device to be inserted into the groove 116 formed along the support 180.

Figure 10B:
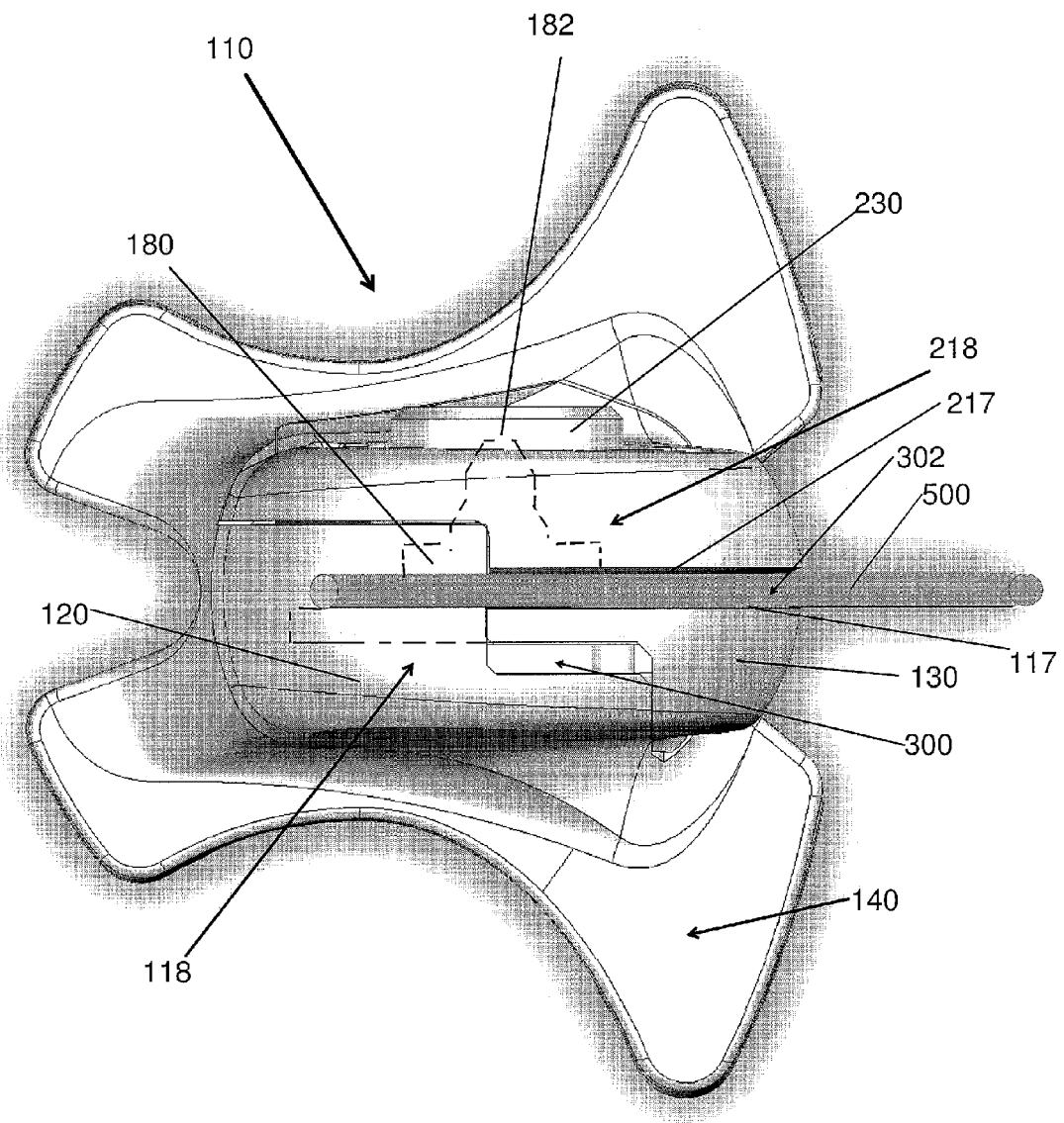
FIG. 10B is a top view of a stabilization device wherein the support portion is in a closed configuration, in accordance with an embodiment of the present invention.
Figure 10C:
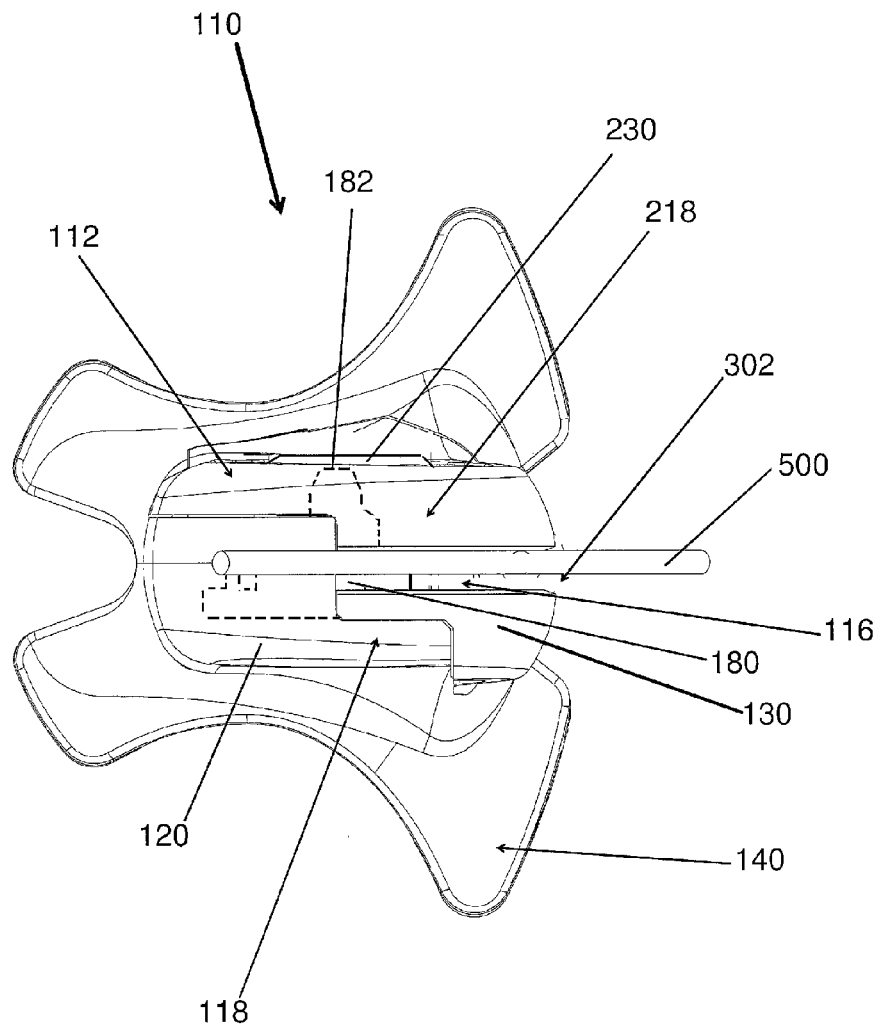
FIGS. 10C-10D are line drawings of the views shown in FIGS. 10A-10B.
Figure 10D:
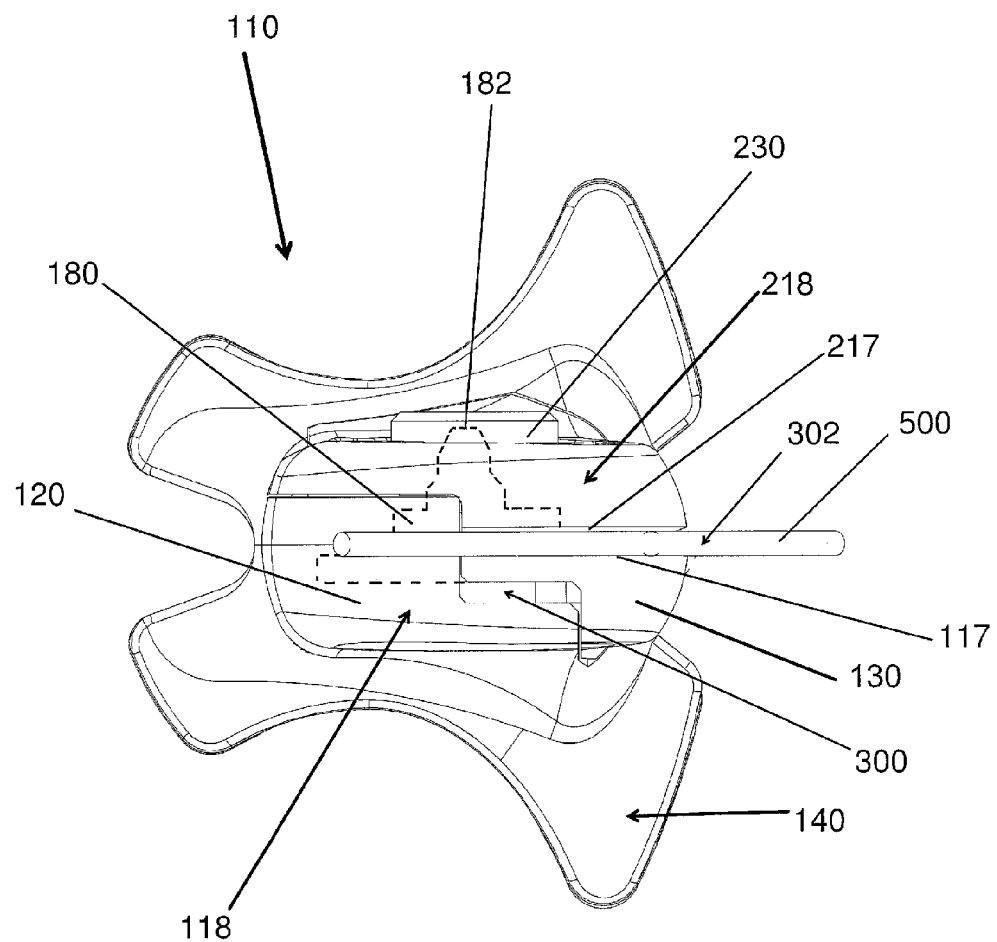

After the medical device has been inserted into the groove 116 at a desired angle of insertion, the button 182 on the support 180 may be released, as illustrated in FIG. 10B. As mentioned previously, the resilient wall portion 230 of the second wall 218 is biased to return to its original position under the absence of an axial force. Thus releasing the button 182 allows the support 180 and moveable wall portion 130 to slide axially away from the fixed wall portion 120, securing the medical device within the groove 116. As the moveable wall portion 130 moves laterally towards the second wall 218, the gap 302 between the moveable wall portion 130 and the second wall 218 decreases and a gap 300 may form between the moveable wall portion 130 and the fixed wall portion 120 The medical device 500 is held firmly within the gap 302 and clamped between the inner wall surfaces 117, 217 of the moveable wall portion 130 and the second wall 218 respectively. The medical device 500 is clamped such that it is held at a specific angle with respect to the vertical axis of the support member 112. In one specific example the medical device 500 is clamped between surfaces 117, 217 of the moveable wall portion 130 and the second wall 218 such that the medical device is fixed at an angle of 45 degrees with respect to the vertical axis.

Figure 11A:
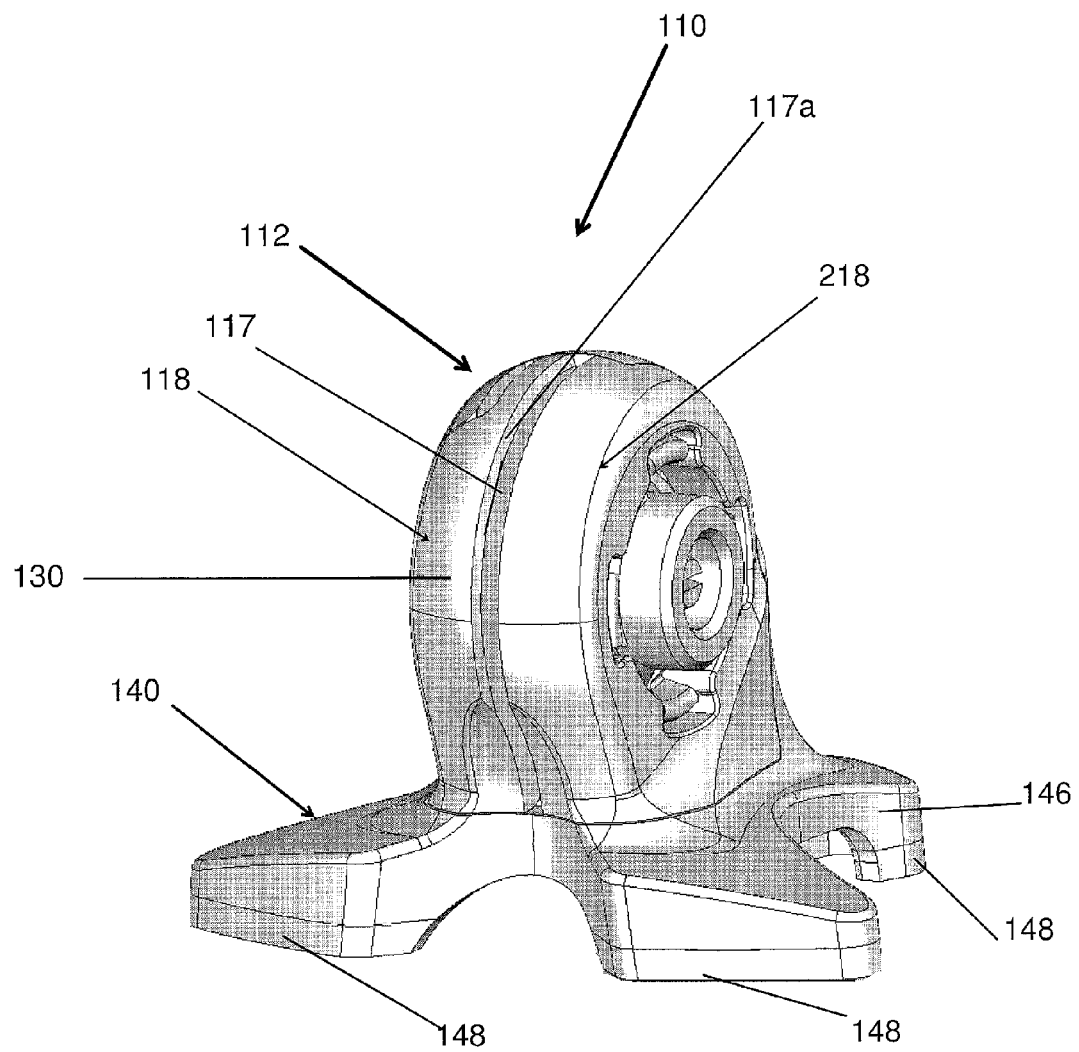
FIG. 11A is a right side perspective view of a stabilization device in accordance with an embodiment of the present invention.
Figure 11B:
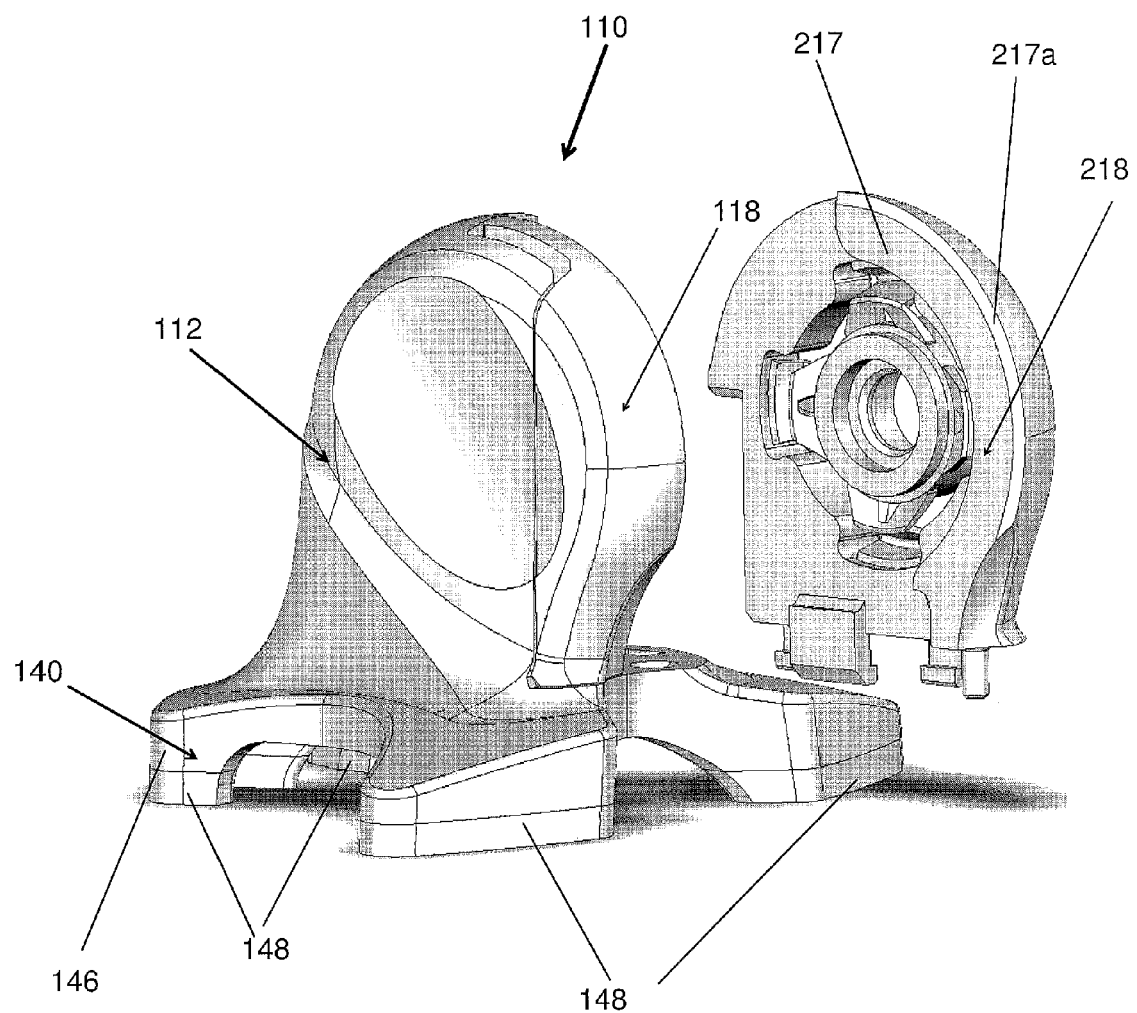
FIG. 11B is a partially exploded view of a stabilization device in accordance with an embodiment of the present invention.
Figure 11C:
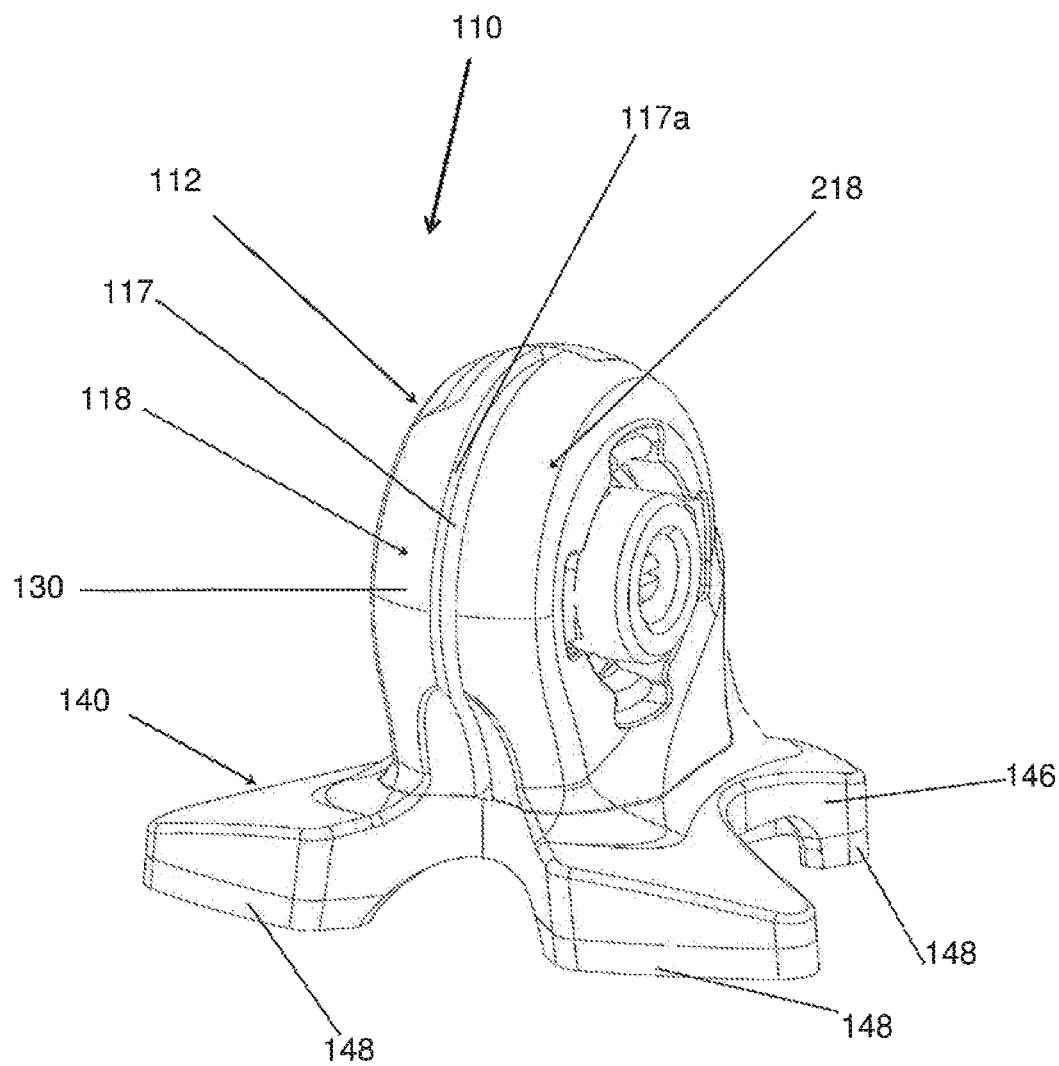
FIGS. 11C-11D are line drawings of the views shown in FIGS. 11A-11B.
Figure 11D:
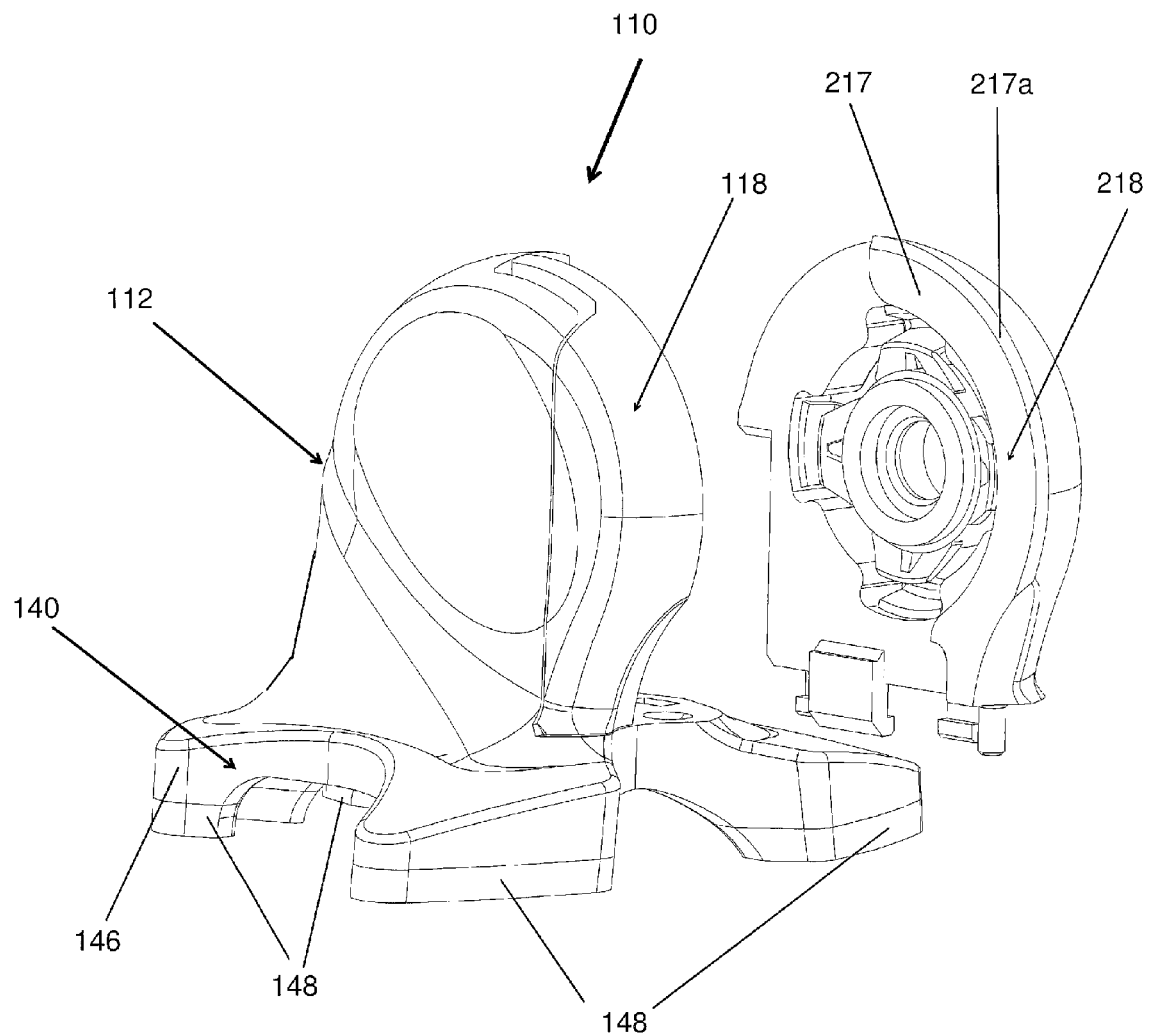

In an embodiment of the present invention, the stabilization device 110 is constructed from a medical grade polymer. The stabilization device 110 may be formed by injection moulding. In one example, the stabilization device is formed through injection moulding of each of the housing 100, the moveable wall portion 130 and the second wall 218. These can then be assembled to form the stabilization device 110. In some embodiments the stabilization device 110 may be constructed from Acrylonitrile Butadiene Styrene (ABS), nylon, polycarbonate or polypropylene. In one specific example, ABS plastic is used. In some embodiments a polymer may be used that provides sufficient flexibility to allow the resilient wall portion 230 to flex when force is applied to it. In one embodiment the moveable wall portion 130 and the second wall portion 218 may comprise a coating of an elastomeric material to increase the ability of the wall portions to grip the medical device 500. The coating is applied to at least a portion of the inner wall surfaces 117, 217. In some embodiments the coating may also be applied to the surface of the groove 119. As discussed previously for other embodiments, the coating may comprise elastomeric materials, including but not limited to, rubbers such as synthetic rubber, thermoplastic elastomer, silicone elastomer and polyurethane elastomer. In some embodiments the elastomer coating may comprise silicone. In one specific example, the silicone is a medical grade silicone. In an alternate embodiment, the elastomer coating may comprise a synthetic rubber such as polychloroprene (neoprene). Alternatively, a thermoplastic elastomer (TPE) such as Santoprene™ may be used. Still furthermore, in some embodiments a Styrene-based thermoplastic elastomer (TPE), may be used to form the coating. In some embodiments the elastomer coating may be overmolded onto the stabilization device. Alternatively, the elastomer coating may be added to the stabilization device through a two-shot moulding process. In an alternate embodiment, the elastomer coating may be applied as a pad that is adhesively attached to the inner wall surfaces 117, 217. In one specific embodiment, the elastomer coating may be applied to the entire surfaces 117 and 217. Alternatively, only a portion of the inner surfaces 117, 217 may be coated. In one embodiment, as illustrated in FIGS. 11A and 11B, the inner surfaces 117 and 217 comprise recessed surfaces 117a and 217a. The coating may be applied within the space defined by the recessed surfaces 117a and 217a. In one specific example, only the surfaces 117a or 217a are coated with the elastomer coating. As mentioned previously, the coating enhances the ability of the wall surfaces 117,217 to grip a medical device. Alternatively, in some embodiments, the inner surfaces 117 and 217 may comprise teeth for gripping the medical device. Similar to the mechanism illustrated in FIGS. 10A and 10B, the stabilization device 110 as shown in FIGS. 11A-11D provides a clamping force between the moveable wall portion 130 and the second wall 218 which allows to grip the medical device firmly between the two wall surfaces 117a and 217a. In one specific example the two surfaces 117a and 217a comprise pads formed from a coating of a styrene-based TPE. The clamping force between the moveable wall portion 130 and the second wall 218 allows to hold a medical device between them and prevents the stabilization device 110 from tipping onto is rear feet 148 attached to the rear legs 146. In the absence of the clamping force the stabilization device may tip back, allowing the medical device to slide through the pads changing the angle at which the medical device is being held. Thus the clamping force provided by the device 110 allows the medical device to be held firmly in place at a desired angle.

Thus, in one broad aspect, embodiments of the present invention comprise a stabilization device for maintaining a position of a medical device relative to a surface of a patient's body, the stabilization device comprising a support portion, said support portion defining a groove for receiving the medical device, the groove structured to allow for positioning of the medical device at a plurality of angles relative to the surface of the patient's body, the groove having opposing wall portions for securing the medical device.

As a feature of this aspect, the groove is a substantially circumferential groove. In one embodiment the groove comprises a plurality of contiguous segments of differing slope.

As a further feature of this aspect, the embodiments of the present invention comprise a stabilization device comprising a base portion, the base portion being attached to a lower surface of said support portion. In one embodiment the base is a quadruped base.

As an additional feature of this aspect, the support portion has an open configuration and a closed configuration. The support portion is operable to receive a medical device within the groove in the open configuration. The support portion is further operable to secure said medical device within said groove in said closed configuration.

The embodiment(s) of the invention described above is (are) intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A stabilization device for maintaining a position of a medical device relative to a surface of a patient's body, the stabilization device comprising:
   a support portion and a base portion attached to a lower surface of the support portion, the base portion configured for placing said stabilization device on the surface of the patient's body, said support portion defining a groove for receiving the medical device, the groove structured to allow for positioning of the medical device at a plurality of angles relative to the surface of the patient's body, the groove defining two opposing walls for securing the medical device, said opposing walls having an open configuration and a closed configuration, said opposing walls being operable to receive a medical device within said groove when in said open configuration and said opposing walls being operable to secure said medical device within said groove in said closed configuration, wherein said opposing walls comprise a first wall and a second wall, said first wall comprising a fixed wall portion and a separate, moveable wall portion detachable from said fixed wall portion, said moveable wall portion being, releasably connected to said second wall said moveable wall portion being operable to slide away from said second wall in said open configuration allowing a medical device to be inserted into a gap formed therebetween, and said moveable wall portion being operable to slide towards said second wall in said closed configuration allowing a medical device to be clamped therebetween said second wall comprising a resilient wall portion, said resilient wall portion being connected to said moveable wall portion by a support said support terminating in a button.

2. The stabilization device of claim 1, wherein said groove is a substantially circumferential groove.

3. The stabilization device of claim 2, wherein said groove is a circular circumferential groove.

4. The stabilization device of claim 2, wherein said groove is a polygonal circumferential groove, wherein said groove comprises a plurality of contiguous segments of differing slope.

5. The stabilization device of claim 1, wherein each of said two opposing walls comprises an inner wall surface.

6. The stabilization device of claim 4, wherein said inner wall surface comprises a plurality of grooves.

7. The stabilization device of claim 5, wherein said inner wall surface has an elastomer coating disposed thereon.

8. The stabilization device of claim 7, wherein said elastomer coating is chosen from the group consisting of: a synthetic rubber, a thermoplastic elastomer, a polyurethane elastomer, a silicone elastomer or silicone.

9. The stabilization device of claim 8, wherein said elastomer coating comprises a thermoplastic elastomer.

10. The stabilization device of claim 8, wherein said elastomer coating comprises a synthetic rubber comprising polychloroprene.

11. The stabilization device of claim 8, wherein said silicone comprises a silicone pad, wherein said silicone pad is adhesively attached to said inner surface.

12. The stabilization device of claim 1, wherein said base portion is substantially rectangular.

13. The stabilization device of claim 1, wherein said base portion comprises a plurality of legs, each of said legs terminating in a foot, wherein said plurality of legs provide both lateral and caudal support.

14. The stabilization device of claim 13, wherein said feet have a height of about 3 mm to about 5 mm.

15. The stabilization device of claim 14, wherein the height of said feet varies along their length.

16. The stabilization device of claim 13, wherein said at least two of said plurality of legs form a channel therebetween, said channel being aligned with said groove, wherein said channel allows the medical device to have unobstructed access to the patient's skin.

17. The stabilization device of claim 16, wherein said channel is an arcuate channel.

18. The stabilization device of claim 13, wherein said feet comprise an elastomer coating disposed on a lower surface of said feet.

19. The stabilization device of claim 18, wherein said elastomer coating is chosen from the group consisting of: a synthetic rubber, a thermoplastic elastomer, a polyurethane elastomer, a silicone elastomer or silicone.

20. The stabilization device of claim 1, wherein said base portion is quadruped.

21. The stabilization device of claim 1, wherein
said resilient wall portion for flexing towards said fixed wall portion when said button is depressed, allowing said moveable wall portion to slide axially away from said second wall and wherein said resilient wall portion retracts towards said second wall when said button is released allowing said moveable wall portion to slide axially towards said second wall.

22. A stabilization device for securing a medical device relative to a surface of a patient's body comprising a support portion and a base portion attached to a lower surface of the support portion, the base portion configured for placing said stabilization device on the surface of the patient's body, said support portion defining a circumferential groove for receiving said medical device, said circumferential groove configured to support said medical device at a plurality of angles, wherein said medical device is held in frictional engagement within said groove, said support portion having an open configuration and a closed configuration, said support portion being operable to receive a medical device within said groove in said open configuration and said support portion being operable to secure said medical device within said groove in said closed configuration, wherein said groove is defined by two opposing walls that comprise a first wall and a second wall, said first wall comprising a fixed wall portion and a separate, moveable wall portion detachable from said fixed wall portion, said moveable wall portion being releasably connected to said second wall, said moveable wall portion being operable to slide away from said second wall in said open configuration allowing a medical device to be inserted into a gap formed therebetween, said moveable wall portion being operable to slide towards said second wall in said closed configuration allowing a medical device to be clamped therebetween, said second wall comprising a resilient wall portion, said resilient wall portion being connected to said moveable wall portion by a support, said support terminating in a button.

23. The stabilization device of claim 22 wherein
said resilient wall portion for flexing towards said fixed wall portion when said button is depressed, allowing said moveable wall portion to slide axially away from said second wall and wherein said resilient wall portion retracts towards said second wall when said button is released allowing said moveable wall portion to slide axially towards said second wall.

24. The stabilization device of claim 22, wherein a radial cross-section of said support is substantially circular.

25. The stabilization device of claim 22, wherein a radial cross-section of said support is substantially cross-shaped.

* * * * *